(12) United States Patent
Hüsler et al.

(10) Patent No.: US 7,642,296 B2
(45) Date of Patent: Jan. 5, 2010

(54) PHOTOINITIATORS

(75) Inventors: Rinaldo Hüsler, Basel (CH); Thomas Horni, Bärschwil (CH); André Fuchs, Schliengen-Obereggenen (DE); Tunja Jung, Rheinfelden-Herten (DE); Reinhard H. Sommerlade, Neuenburg am Rhein (DE)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 271 days.

(21) Appl. No.: 11/578,595

(22) PCT Filed: Apr. 11, 2005

(86) PCT No.: PCT/EP2005/051576
§ 371 (c)(1),
(2), (4) Date: Oct. 16, 2006

(87) PCT Pub. No.: WO2005/100292
PCT Pub. Date: Oct. 27, 2005

(65) Prior Publication Data
US 2007/0240609 A1    Oct. 18, 2007

(30) Foreign Application Priority Data
Apr. 19, 2004    (EP) ................... 04101592

(51) Int. Cl.
*C08F 2/50* (2006.01)
*C03C 25/10* (2006.01)
*C07C 49/84* (2006.01)

(52) U.S. Cl. .............. 522/6; 522/33; 522/42; 522/44; 522/113

(58) Field of Classification Search ............ 522/6, 522/33, 113, 42, 44
See application file for complete search history.

(56) References Cited

U.S. PATENT DOCUMENTS
4,284,485 A * 8/1981 Berner .............. 522/42
(Continued)

FOREIGN PATENT DOCUMENTS
WO    02/100903    12/2002
(Continued)

OTHER PUBLICATIONS
Baudin et al. PCT/EP01/14354 Jun. 2002.*

*Primary Examiner*—David Wu
*Assistant Examiner*—Jessica Paul
(74) *Attorney, Agent, or Firm*—Joseph C. Suhadolnik

(57) ABSTRACT

The invention relates to novel photoinitators of formulae (I), (II), (III), (IV), (V) and (VI) wherein $R_1$ and $R_2$ are each independently of the other $C_1$-$C_8$alkyl; $C_1$-$C_4$alkyl substituted by OH, $C_1$-$C_4$alkoxy, —COO($C_1$-$C_8$alkyl), ($C_1$-$C_4$alkyl)-COO—, —CN, benzyl, phenyl or by —N($R_{15}$) ($R_{16}$); $C_3$-$C_6$alkerlyl, benzyl, —$CH_2$—$C_6H_4$—($C_1$-$C_4$alkyl) or phenyl; or $R_1$ and $R_2$ together are unbranched or branched $C_2$-$C_9$alkylene or $C_3$-$C_6$-oxa- or -azaalkylene; $R_3$, $R_4$, $R_5$ and $R_6$ are each independently of the others hydrogen, $C_1$-$C_8$alkyl, $C_3$-$C_6$alkenyl, benzyl, —$CH_2$—$C_6H_4$—($C_1$-$C_4$alkyl) or phenyl; $R_3$ and $R_4$ together and/or $R_5$ and $R_6$ together are unbranched or branched $C_2$-$C_9$alkylene; A is Cl, Br, —O—$R_9$, —N($R_{11}$)($R_{12}$) or —S—$R_{18}$, A' is —O—, —NH— or —$NR_{11}$—; A" is Cl, Br, —O—$R_9$, —N($R_{11}$) ($R_{12}$) or —S—$R_{18}$ or hydrogen, X is —O—$R_{10}$ or —N($R_{13}$) ($R_{14}$), n is an integer from 1 to 10, preferably an integer from 1 to 4, especially 1, 2 or 3; $R_7$ is a linker; $R_8$ is a bivalent $C_2$-$C_3$alkylele radical.

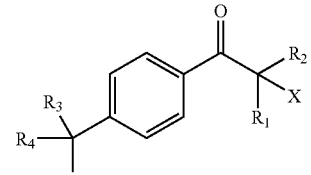

(I)

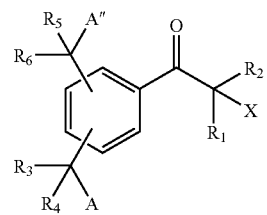

(II)

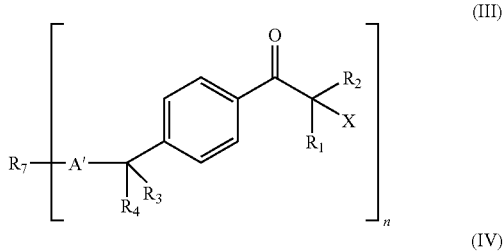

(III)

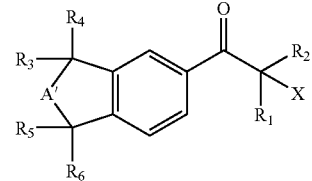

(IV)

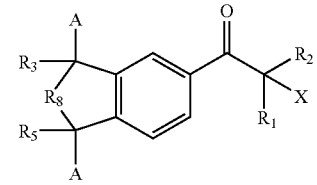

(V)

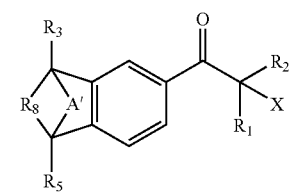

(VI)

9 Claims, No Drawings

U.S. PATENT DOCUMENTS

| | | | |
|---|---|---|---|
| 4,534,838 A * | 8/1985 | Lin et al. | 522/33 |
| 4,861,916 A | 8/1989 | Köhler et al. | 568/337 |
| 6,204,302 B1 | 3/2001 | Rawls et al. | 522/8 |
| 6,441,244 B1 | 8/2002 | Avar et al. | 568/327 |
| 7,084,183 B2 * | 8/2006 | Fuchs et al. | 522/36 |
| 2003/0236425 A1 | 12/2003 | Herr et al. | 556/443 |
| 2004/0073068 A1 | 4/2004 | Joo et al. | 568/319 |
| 2004/0170924 A1 | 9/2004 | Kunimoto et al. | 430/281.1 |
| 2004/0204613 A1 | 10/2004 | Wolf et al. | 568/14 |
| 2005/0020712 A1 | 1/2005 | Baudin et al. | 522/37 |
| 2005/0119435 A1 | 6/2005 | Baudin et al. | 528/25 |
| 2005/0228062 A1 | 10/2005 | Wolf et al. | 522/6 |

FOREIGN PATENT DOCUMENTS

| | | |
|---|---|---|
| WO | 03/019295 | 3/2003 |
| WO | 03/066687 | 8/2003 |
| WO | 03/066688 | 8/2003 |
| WO | 03/091287 | 11/2003 |
| WO | 04/000889 | 12/2003 |

* cited by examiner

PHOTOINITIATORS

The invention relates to novel photoinitiators and to mixtures thereof for radiation-curable compositions, especially using ultraviolet and visible radiation, to intermediates for their preparation and to a process for the preparation of the initiators from the intermediates.

Radiation-curable systems can be used in a large number of applications, for example in overprint varnishes, printing inks, in the manufacture of electronic printed circuit boards and printing plates, and in the coating of various substrates, such as wood, plastics, paper, glass or metal. For efficient polymerisation of such systems, it is necessary to use a photoinitiator, from which, as a result of interaction with electromagnetic radiation, reactive particles such as free radicals or cations (protons) are generated. A disadvantage of most of the initiators frequently used in practice is the undesirable odour that is produced when they are used. There is therefore a demand in the art for low-odour, low-volatility photoinitiators. In addition, it is desirable for the photoinitiator to contribute towards an improved crosslinking density and to produce fewer photolysis products that are capable of migration. Moreover, the photoinitiator should be available in an easy-to-handle form, should cause minimal yellowing of the cured film, and should be readily soluble in radiation-curable formulations. A further important criterion for the use of photoinitiators is the effectiveness with which the reactive constituents of the formulation are polymerised. This has a direct effect on the curing speed which can be achieved during use, and on the degree of crosslinking of the resulting polymer.

European Patent EP-B-216 884 describes photoinitiators such as, for example, Irgacure 2959: 2-hydroxy-1-[4-(2-hydroxy-ethoxy)-phenyl]-2-methyl-propan-1-one.

U.S. Pat. No. 4,861,916 describes α-hydroxy ketones of formula HO—CH$_2$—CH$_2$-phenyl-CO—C(CH$_3$)(CH$_3$)—OH. There are at least two CH$_2$ groups between the phenyl ring and the OH group.

It has now been found that o-hydroxy ketones, x-alkoxy ketones and α-amino ketones of the following formulae possess the required properties as photoinitiators and, compared with Irgacure 2959, have higher reactivity at the benzylic hydroxy group and do not have a tendency to yellowing.

The invention accordingly relates to novel photoinitiators of formulae I, II, III, IV, V and VI

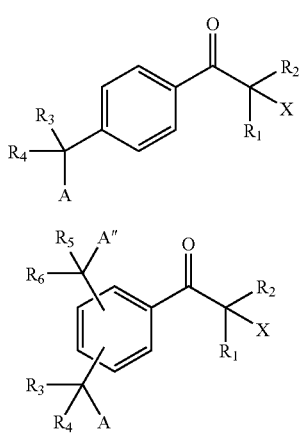

I

II

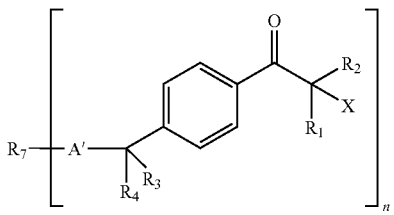

III

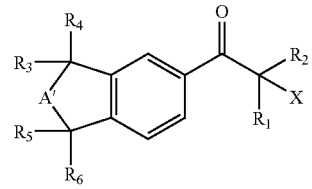

IV

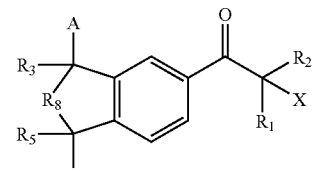

V

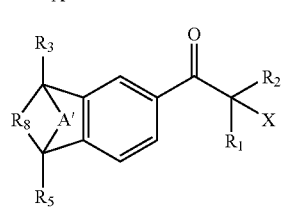

VI wherein
R$_1$ and R$_2$ are each independently of the other C$_1$-C$_8$alkyl; C$_1$-C$_4$alkyl substituted by OH, C$_1$-C$_4$alkoxy, —COO(C$_1$-C$_8$alkyl), (C$_1$-C$_4$alkyl)-COO—, —CN, benzyl, phenyl or by —N(R$_{15}$)(R$_{16}$); C$_3$-C$_6$alkenyl, benzyl, —CH$_2$—C$_6$H$_4$—(C$_1$-C$_4$alkyl) or phenyl; or
R$_1$ and R$_2$ together are unbranched or branched C$_2$-C$_9$alkylene or C$_3$-C$_6$-oxa- or -aza-alkylene;
R$_3$, R$_4$, R$_5$ and R$_6$ are each independently of the others hydrogen, C$_1$-C$_8$alkyl, C$_3$-C$_6$alkenyl, benzyl, —CH$_2$—C$_6$H$_4$—(C$_1$-C$_4$alkyl) or phenyl;
R$_3$ and R$_4$ together and/or R$_5$ and R$_6$ together are unbranched or branched C$_2$-C$_9$alkylene;
A is Cl, Br, —O—R$_9$, —N(R$_{11}$)(R$_{12}$) or —S—R$_{18}$,
A' is —O—, —NH— or —NR$_{11}$—;
A" is Cl, Br, —O—R$_9$, —N(R$_{11}$)(R$_{12}$) or —S—R$_{18}$ or hydrogen,
X is —O—R$_{10}$ or —N(R$_{13}$)(R$_{14}$),
n is an integer from 1 to 10, preferably an integer from 1 to 4, especially 1, 2 or 3;
R$_7$ is an n-valent linear or branched C$_2$-C$_{20}$alkyl radical the carbon chain of which may be interrupted by cyclohexanediyl, phenylene, —CH(OH)—, —C(C$_2$H$_5$)(CH$_2$—CH$_2$—OH)—, —C(CH$_3$)(CH$_2$—CH$_2$—OH)—, —C(CH$_2$—CH$_2$—OH)$_2$—, —N(CH$_3$)—, —N(C$_2$H$_5$)—, —N(CH$_2$—CH$_2$—OH)—, —CO—O—, —O—CO—, —P(CH$_2$—CH$_2$—OH)—, —P(O)(CH$_2$—CH$_2$—OH)—, —O—P(O—CH$_2$—CH$_2$—OH)—O—, —O—P(O)(O—CH$_2$—CH$_2$—OH)—O—, —O-cyclohexanediyl-C(CH$_3$)$_2$-cyclohexanediyl-O—, —O-phenylene-C(CH$_3$)$_2$-phenylene-O—, —O-phenylene-CH$_2$-phenylene-O—, —Si(CH$_3$)$_2$—, —O—Si(CH$_3$)$_2$—O—, —O—Si(CH$_3$)(O—CH$_3$)—O—, —Si(CH$_3$)(R$_{19}$)—O—Si(CH$_3$)(R$_{20}$)—, 5-(2-hydroxy-ethyl)-[1,3,5]triazinane-2,4,6-trione-1,3-diyl and/or by from one to nine oxygen atoms, or R$_7$ is an n-valent linear or branched —CO—NH—(C$_2$-C$_{12}$alkylene)-(NH—CO)$_{n-1}$— or linear or branched —CO—NH—(C$_0$-C$_{12}$alkylene)-(NH—CO)$_{n-1}$— radical which may be interrupted by one or two phenylene, methylphenylene, phenylene-O-phenylene, cyclohexanediyl, methylcyclohexanediyl, trimethylcyclohexanediyl, norbornanediyl, [1-3]diazetidine-2,4-dione-1,3-diyl, 3-(6-isocyanatohexyl)-biuret-1,5-diyl or 5-(6-isocyanatohexyl)-[1,3,5]tri-azinane-2,4,6-trione-1,3-diyl radical(s), or R$_7$ is an n-valent linear or branched —CO—(C$_0$-C$_{12}$alkylene)-(CO)$_{n-1}$— radical and the alkylene may be interrupted by oxygen, phenylene, cyclohexanediyl or by norbornanediyl;

R$_8$ is a bivalent C$_2$-C$_3$alkylene radical,

R$_9$ is hydrogen, —Si(C$_1$-C$_6$alkyl)$_3$, C$_1$-C$_{12}$alkyl, R$_{23}$, C$_2$-C$_{18}$acyl, —CO—NH—C$_1$-C$_{12}$alkyl, —CO—C$_1$-C$_4$alkoxy, C$_2$-C$_{20}$hydroxyalkyl, C$_2$-C$_{20}$methoxyalkyl, 3-(C$_1$-C$_{18}$alkoxy)-2-hydroxy-propyl, 3-[1,3,3,3-tetramethyl-1-[(trimethylsilyl)oxy]disiloxanyl]-propyl, 2,3-dihydroxy-propyl or linear or branched C$_2$-C$_{21}$hydroxyalkyl or (C$_1$-C$_4$alkoxy)-C$_2$-C$_{21}$alkyl the carbon chain of which is interrupted by from one to nine oxygen atoms, R$_{10}$ is hydrogen, —Si(C$_1$-C$_6$alkyl)$_3$, C$_2$-C$_8$alkyl, C$_3$-C$_6$alkenyl or benzyl, R$_{11}$ and R$_{12}$ are each independently of the other hydrogen, C$_1$-C$_{12}$alkyl, R$_{23}$; C$_2$-C$_4$alkyl substituted by one or more of the groups OH, C$_1$-C$_4$alkoxy, —CN and —COO(C$_1$-C$_4$alkyl); C$_3$-C$_5$alkenyl, cyclohexyl or C$_7$-C$_9$phenylalkyl, or R$_{11}$ and R$_{12}$ together are unbranched or branched C$_3$-C$_9$alkylene which may be interrupted by —O— or by —N(R$_{17}$)—, R$_{13}$ and R$_{14}$ are each independently of the other C$_1$-C$_{12}$alkyl; C$_2$-C$_4$alkyl substituted by one or more of the groups OH, C$_1$-C$_4$alkoxy, —CN and —COO(C$_1$-C$_4$alkyl); C$_3$-C$_5$alkenyl, cyclohexyl or C$_7$-C$_9$phenylalkyl, or R$_{13}$ and R$_{14}$ together are unbranched or branched C$_3$-C$_9$alkylene which may be interrupted by —O— or by —N(R$_{17}$)—, R$_{15}$ and R$_{16}$ are each independently of the other hydrogen, C$_1$-C$_{12}$alkyl; C$_2$-C$_4$alkyl substituted by one or more of the groups OH, C$_1$-C$_4$alkoxy, —CN and —COO(C$_1$-C$_4$alkyl); C$_3$-C$_5$-alkenyl, cyclohexyl or C$_7$-C$_9$phenylalkyl, or R$_{15}$ and R$_{16}$ together are unbranched or branched C$_3$-C$_9$alkylene which may be interrupted by —O— or by —N(R$_{17}$)—, R$_{17}$ is hydrogen, C$_1$-C$_4$alkyl, allyl, benzyl, C$_1$-C$_4$hydroxyalkyl, —CH$_2$CH$_2$—COO(C$_1$-C$_4$alkyl) or —CH$_2$CH$_2$CN, R$_{18}$ is C$_1$-C$_{18}$alkyl, hydroxyethyl, 2,3-dihydroxypropyl, cyclohexyl, benzyl, phenyl, C$_1$-C$_{12}$alkylphenyl, —CH$_2$—COO(C$_1$-C$_{18}$alkyl), —CH$_2$CH$_2$—COO(C$_1$-C$_{18}$alkyl) or —CH(CH$_3$)—COO(C$_1$-C$_{18}$alkyl), R$_{19}$ and R$_{20}$ are each independently of the other a monovalent radical methyl, —O—Si(CH$_3$)$_3$, —O—Si(CH$_3$)$_2$—O—Si(CH$_3$)$_3$, —O—Si(CH$_3$)[—(CH$_2$)$_p$—OH]—O—Si(CH$_3$) or a bivalent radical —O—Si(CH$_3$)$_2$—, —O—Si(CH$_3$)[—(CH$_2$)$_p$—OH]—, —O—Si(CH$_3$)(R$_{21}$)—, —O—Si(CH$_3$)(R$_{22}$)— and form chains, R$_{21}$ and R$_{22}$ are each independently of the other a monovalent radical methyl, —O—Si(CH$_3$)$_3$, —O—Si(CH$_3$)$_2$—O—Si(CH$_3$)$_3$, —O—Si(CH$_3$)[—(CH$_2$)$_p$—OH]-O—Si(CH$_3$) or a bivalent radical —O—Si(CH$_3$)$_2$—, —O—Si(CH$_3$)[—(CH$_2$)$_p$—OH]—, —O—Si(CH$_3$)(R$_{21}$)—, —O—Si(CH$_3$)(R$_{22}$)— and extend chains, and, when R$_{21}$ and R$_{22}$ are linked to form a ring, —(R$_{21}$)—(R$_{22}$)— is the bridge —O—, R$_{23}$ is, independently of formula I, a radical

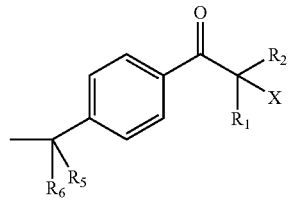

p is an integer from 2 to 12, preferably 3, 5 or 6, it being possible for the carbon chain of the alkylene to be interrupted by from one to three oxygen atoms.

Alkyl may be unbranched or branched alkyl.

C$_3$-C$_6$Alkenyl is, for example, allyl, methallyl or 2-butenyl.

When R$_1$ and R$_2$ together and/or R$_3$ and R$_4$ together are C$_3$-C$_6$-oxa- or -aza-alkylene, there is formed, for example, an aziridine, azetidine, pyrrolidine, imidazolidine, piperidine, piperazine or morpholine ring.

C$_2$-C$_{18}$Acyl is, for example, acetyl, propanoyl, butanoyl, 2-methylpropanoyl, butanoyl to octadecanoyl.

Hydroxyalkyl is alkyl substituted by hydroxy.

Hydroxyalkyl interrupted by from one to nine oxygen atoms is, for example, —(CH$_2$)$_a$—O—(CH$_2$)$_b$—OH.

Preferred Compounds:

Photoinitiators of formula I, II, III, IV, V or VI as defined hereinbefore wherein R$_1$ and R$_2$ are each independently of the other C$_1$-C$_8$alkyl, C$_3$-C$_6$alkenyl, benzyl, —CH$_2$—C$_6$H$_4$—(C$_1$-C$_4$alkyl) or phenyl, or R$_1$ and R$_2$ together are unbranched or branched C$_2$-C$_9$alkylene;

R$_3$, R$_4$, R$_5$ and R$_6$ are each independently of the others hydrogen, C$_1$-C$_8$alkyl, C$_3$-C$_6$alkenyl, benzyl, —CH$_2$—C$_6$H$_4$—(C$_1$-C$_4$alkyl) or phenyl;

R$_3$ and R$_4$ together and/or R$_5$ and R$_6$ together are unbranched or branched C$_3$-C$_9$alkylene;

A is Cl, Br, —O—R$_9$ or —N(R$_{11}$)(R$_{12}$),

A' is —O—;

A" is Cl, Br, —O—R$_9$—N(R$_{11}$)(R$_{12}$) or hydrogen;

X is —O—R$_{10}$ or —N(R$_{13}$)(R$_{14}$), n is 1, 2 or 3;

R$_7$, R$_8$, R$_9$, R$_{10}$, R$_{11}$, R$_{12}$, R$_{13}$, R$_{14}$, R$_{17}$, R$_{19}$, R$_{20}$, R$_{21}$, R$_{22}$ and R$_{23}$ are as defined hereinbefore.

Photoinitiators of formulae I and II wherein

R$_1$ and R$_2$ are methyl, or R$_1$ and R$_2$ together are C$_5$alkylene;

R$_3$, R$_4$, R$_5$ and R$_6$ are each independently of the others hydrogen, C$_1$-C$_8$alkyl, C$_3$-C$_6$alkenyl, benzyl, —CH$_2$—C$_6$H$_4$—(C$_1$-C$_4$alkyl) or phenyl;

R$_3$ and R$_4$ together and/or R$_5$ and R$_6$ together are unbranched or branched C$_3$-C$_9$alkylene;

A is —O—R$_9$ or —N(R$_{11}$)(R$_{12}$),

A" is —O—R$_9$, —N(R$_{11}$)(R$_{12}$) or hydrogen;

X is —OH or —N(R$_{13}$)(R$_{14}$), $R_9$ is hydrogen, —Si(CH$_3$)$_3$, $C_1$-$C_8$alkyl, 4-(2-hydroxy-2-methyl-propionyl)-benzyl, 4-(1-hydroxy-cyclohexanecarbonyl)-benzyl, $C_2$-$C_{18}$acyl, —CO—NH—$C_1$-$C_8$alkyl, —CO—$C_1$-$C_4$-alkoxy, $C_2$-$C_{20}$hydroxyalkyl, $C_2$-$C_{20}$methoxyalkyl or $C_2$-$C_{20}$hydroxyalkyl the carbon chain of which is interrupted by from one to nine oxygen atoms;

$R_9$ for formula II has one of the meanings hydrogen, —Si(CH$_3$)$_3$, $C_1$-$C_8$alkyl, 4-(2-hydroxy-2-methyl-propionyl)-benzyl, 2-hydroxymethyl-4-(2-hydroxy-2-methyl-propionyl)-benzyl, 2-methyl-4-(2-hydroxy-2-methyl-propiony)-benzyl, 4-(1-hydroxy-cyclohexanecarbonyl)-benzyl, 2-hydroxymethyl-4-(1-hydroxy-cyclohexanecarbonyl)-benzyl, 2-methyl-4-(1-hydroxy-cyclohexanecarbonyl)-benzyl, $C_2$-$C_{18}$acyl, —CO—NH—$C_1$-$C_8$alkyl, $C_2$-$C_{20}$-hydroxyalkyl, $C_2$-$C_{20}$methoxyalkyl or $C_2$-$C_{20}$hydroxyalkyl the carbon chain of which is interrupted by from one to nine oxygen atoms;

$R_{11}$ and $R_{12}$ and $R_{13}$ and $R_{14}$ are as defined hereinbefore.

Photoinitiators of formulae I and II wherein $R_1$ and $R_2$ are methyl, or $R_1$ and $R_2$ together are $C_5$alkylene;

X is OH;

$R_3$, $R_4$, $R_5$ and $R_6$ are each independently of the others hydrogen or $C_1$-$C_6$alkyl;

$R_3$ and $R_4$ together and/or $R_5$ and $R_6$ together are unbranched or branched $C_4$-$C_9$alkylene;

A is —OH or —OH—CH$_3$;

A" is —OH or —OH—CH$_3$ or hydrogen.

Photoinitiators of formulae I and III (dimer forms) wherein $R_1$ and $R_2$ are methyl, or $R_1$ and $R_2$ together are $C_5$alkylene;

$R_3$, $R_4$, $R_5$ and $R_6$ are hydrogen;

n is an integer from 1 to 3, especially 2;

A is 4-(2-hydroxy-2-methyl-propionyl)-benzyl or 4-(1-hydroxy-cyclohexanecarbonyl)-benzyl;

A' is —O—;

X is hydroxy;

$R_7$ is an n-valent linear or branched $C_2$-$C_{12}$alkyl radical the carbon chain of which may be interrupted by cyclohexanediyl, phenylene, —CH(OH)—, —C(C$_2$H$_5$)(CH$_2$—CH$_2$—OH)—, —C(CH$_3$)(CH$_2$—CH$_2$—OH)—, —C(CH$_2$—CH$_2$—OH)$_2$—, —N(CH$_3$)—, —N(C$_2$H$_5$)—, —N(CH$_2$—CH$_2$—OH)—, —CO—O—, —O—CO—, —O-cyclohexanediyl-C(CH$_3$)$_2$-cyclohexanediyl-O—, —O-phenylene-C(CH$_3$)$_2$-phenylene-O—, —O-phenylene-CH$_2$-phenylene-O—, —Si(CH$_3$)$_2$—, —O—Si(CH$_3$)$_2$—O—, —O—Si(CH$_3$)(O—CH$_3$)—O—, and/or by from one to nine oxygen atoms, or $R_7$ is an n-valent linear or branched —CO—NH—(C$_2$-C$_{12}$alkylene)-(NH—CO)$_{n-1}$— or linear or branched —CO—NH—(C$_0$-C$_{12}$alkylene)-(NH—CO)$_{n-1}$— radical wherein the carbon chain of the radicals may be interrupted by one or two phenylene, methylphenylene, phenylene-O-phenylene, cyclohexanediyl, methylcyclohexanediyl, trimethylcyclohexanediyl, norbornanediyl, [1-3]diazetidine-2,4-dione-1,3-diyl or 5-(6-isocyanatohexyl)-[1,3,5]triazinane-2,4,6-trione-1,3-diyl radical(s), or $R_7$ is an n-valent linear or branched —CO—(C$_0$-C$_{12}$alkylene)-(CO)$_{n-1}$— radical and the carbon chain of which may be interrupted by oxygen, phenylene, cyclohexanediyl or by norbornanediyl.

The radical $R_7$ is preferably prepared from alcohols from the following list:

Collection of structures for technical di- and oligo-alcohols

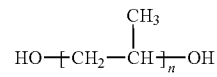

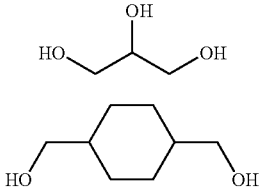

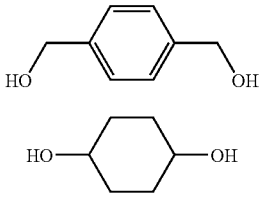

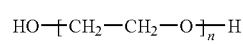

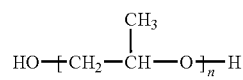

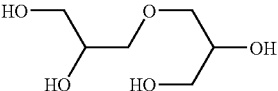

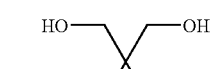

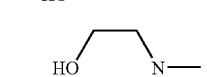

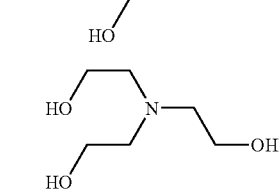

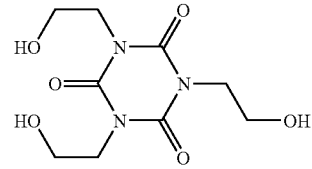

-continued
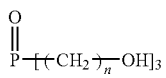
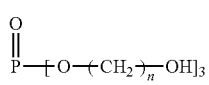
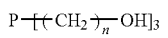
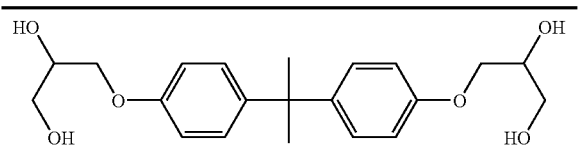
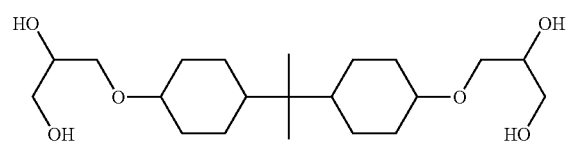
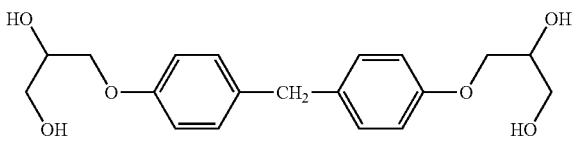
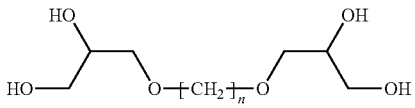
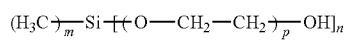
n > 0
n + m = 4
p = 1-6
[(H$_3$C)$_3$—Si—O)$_2$—Si(CH$_3$)—(CH$_2$)$_3$—OH
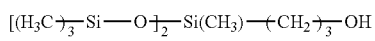
n > 0
n + m = 4
p = 1-2
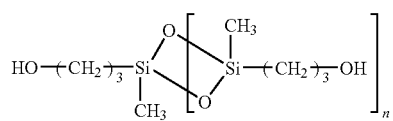
n = 3, 4
(H$_3$C)$_m$—Si—[(CH$_2$)$_3$—(O—CH$_2$—CH$_2$)$_p$—OH]$_n$
n > 0
n + m = 4
p = 1-4
-continued
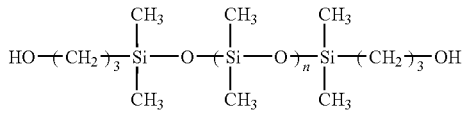
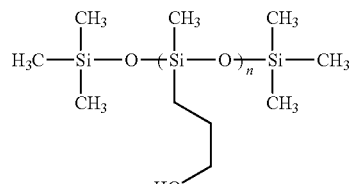
The radical R$_7$ is prepared from isocyanates from the following list:
Collection of structures for technical di- and oligo-isocyanates
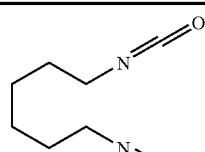
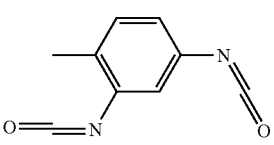
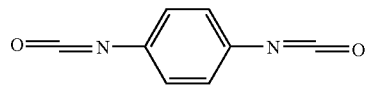
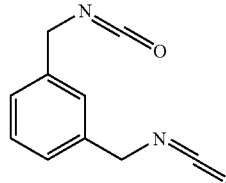
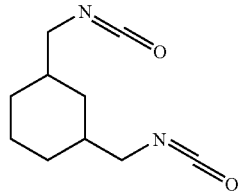
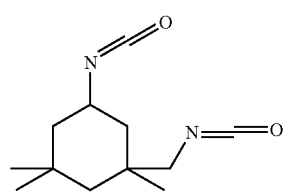

-continued
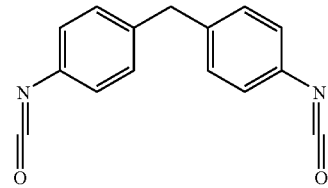
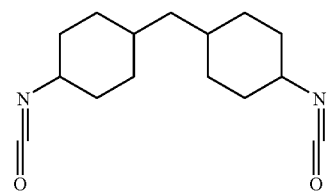
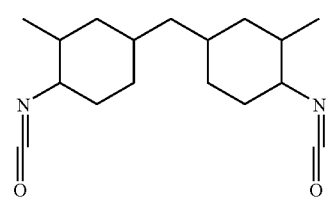
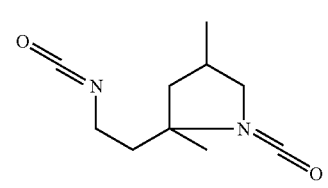
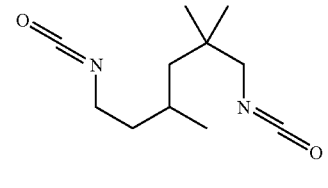
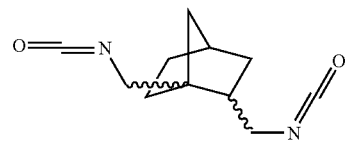
2,5-2,6 exo/endo
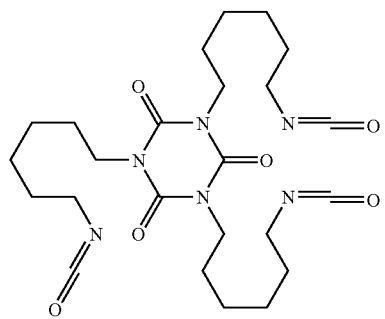
-continued
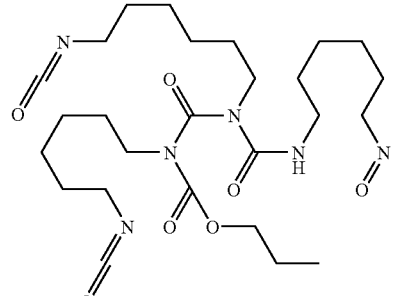
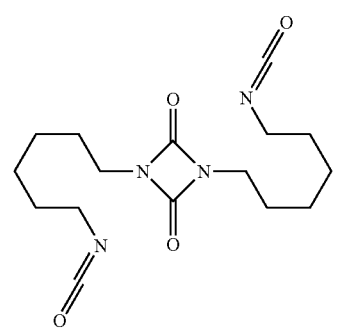
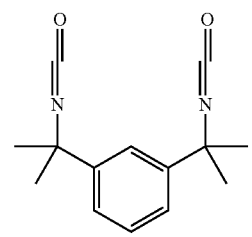
Collection of structures for technical di and polycarboxylic acids.
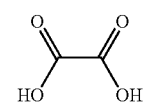
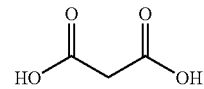
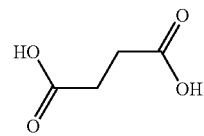
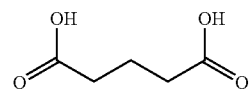

-continued

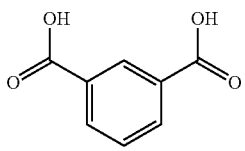

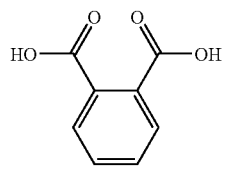

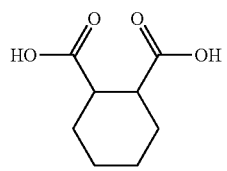

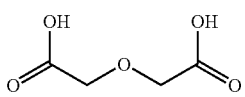

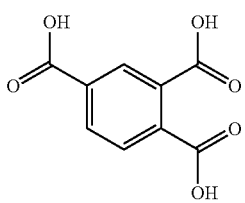

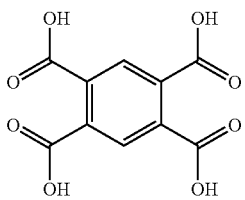

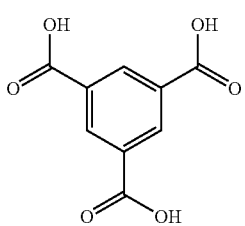

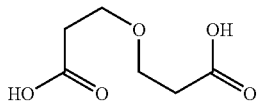

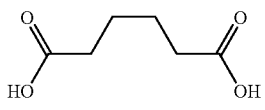

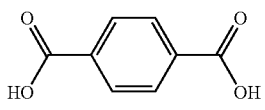

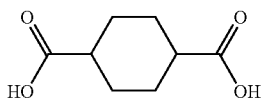

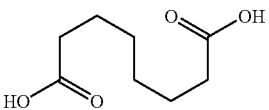

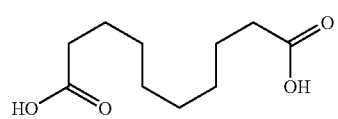

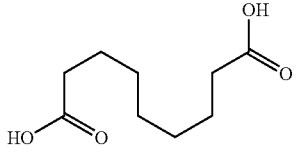

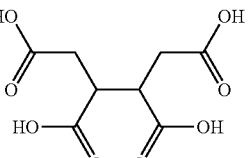

EXAMPLES OF COMPOUNDS OF FORMULA I ARE

2-Hydroxy-1-(4-hydroxymethyl-phenyl)-2-methyl-propan-1-one
2-Hydroxy-1-(4-methoxymethyl-phenyl)-2-methyl-propan-1-one
1-(4-Methoxymethyl-phenyl)-2-methyl-2-morpholin-4-yl-propan-1-one
2-Methyl-2-morpholin-4-yl-1-(4-morpholin-4-ylmethyl-phenyl)-propan-1-one
2-Hydroxy-1-{4-[2-(2-hydroxy-ethoxy)-ethoxymethyl]-phenyl}-2-methyl-propan-1-one
2-Hydroxy-1-(4-{2-[2-(2-hydroxy-ethoxy)-ethoxy]-ethoxymethyl}-phenyl)-2-methyl-propan-1-one
2-Hydroxy-1-[4-(2-{2-[2-(2-hydroxy-ethoxy)-ethoxy]-ethoxy}-ethoxymethyl)-phenyl]-2-methyl-propan-1-one
1-(4-Bromomethyl-phenyl)-2-hydroxy-2-methyl-propan-1-one
1-(4-Chloromethyl-phenyl)-2-hydroxy-2-methyl-propan-1-one
2-Hydroxy-2-methyl-1-(4-morpholin-4-ylmethyl-phenyl)-propan-1-one
Carbonic acid 4-(2-hydroxy-2-methyl-propionyl)-benzyl ester methyl ester 2-Hydroxy-1-{4-[4-(2-hydroxy-2-methyl-propionyl)-benzyloxymethyl]-phenyl}-2-methyl-propan-1-one
2-Hydroxy-1-[4-(1-hydroxy-2-methyl-propyl)-phenyl]-2-methyl-propan-1-one
2-Hydroxy-1-[4-(1-methoxy-2-methyl-propyl)-phenyl]-2-methyl-propan-1-one
2-Hydroxy-2-methyl-1-[4-(2-methyl-1-methylamino-propyl)-phenyl]-propan-1-one
1-[4-(1-Dimethylamino-2-methyl-propyl)-phenyl]-2-hydroxy-2-methyl-propan-1-one
2-Hydroxy-2-methyl-1-[4-(2-methyl-1-morpholin-4-yl-propyl)-phenyl]-propan-1-one
2-Hydroxy-1-[4-(1-hydroxy-1-methyl-ethyl)-phenyl]-2-methyl-propan-1-one
2-Hydroxy-1-[4-(hydroxy-phenyl-methyl)-phenyl]-2-methyl-propan-1-one
2-Hydroxy-1-[4-(methoxy-phenyl-methyl)-phenyl]-2-methyl-propan-1-one
2-Hydroxy-2-methyl-1-[4-(methylamino-phenyl-methyl)-phenyl]-propan-1-one
2-Hydroxy-1-(4-{[(2-hydroxy-ethyl)-methyl-amino]-phenyl-methyl}-phenyl)-2-methyl-propan-1-one
1-(4-{[Bis-(2-hydroxy-ethyl)-amino]-phenyl-methyl}-phenyl)-2-hydroxy-2-methyl-propan-1-one
1-(4-Dimethylaminomethyl-phenyl)-2-hydroxy-2-methyl-propan-1-one
2-Hydroxy-2-methyl-1-(4-methylaminomethyl-phenyl)-propan-1-one
1-(4-Ethylaminomethyl-phenyl)-2-hydroxy-2-methyl-propan-1-one
1-(4-Butylaminomethyl-phenyl)-2-hydroxy-2-methyl-propan-1-one
1-(4-Hexylaminomethyl-phenyl)-2-hydroxy-2-methyl-propan-1-one
1-(4-Dodecylaminomethyl-phenyl)-2-hydroxy-2-methyl-propan-1-one
2-Hydroxy-1-(4-{[(2-hydroxy-ethyl)-methyl-amino]-methyl}phenyl)-2-methyl-propan-1-one
1-(4-{[Bis-(2-hydroxy-ethyl)-amino]-methyl}-phenyl)-2-hydroxy-2-methyl-propan-1-one
2-Hydroxy-1-{4-[(2-hydroxy-propylamino)-methyl]-phenyl}-2-methyl-propan-1-one
2-Benzyl-2-dimethylamino-1-(4-morpholin-4-ylmethyl-phenyl)-butan-1-one
2-Dimethylamino-1-(4-dimethylaminomethyl-phenyl)-2-(4-methyl-benzyl)-butan-1-one
2-Dimethylamino-2-ethyl-1-(4-{[(2-hydroxy-ethyl)-methyl-amino]-methyl}-phenyl)-pent-4-en-1-one
1-(4-Ethoxymethyl-phenyl)-2-hydroxy-2-methyl-propan-1-one
1-(4-Butoxymethyl-phenyl)-2-hydroxy-2-methyl-propan-1-one
2-Hydroxy-1-[4-(2-methoxy-ethoxymethyl)-phenyl]-2-methyl-propan-1-one
2-Hydroxy-1-[4-(4-hydroxy-butoxymethyl)-phenyl]-2-methyl-propan-1-one
2-Hydroxy-1-[4-(6-hydroxy-hexyloxymethyl)-phenyl]-2-methyl-propan-1-one
2-Hydroxy-1-[4-(2-hydroxy-propoxymethyl)-phenyl]-2-methyl-propan-1-one
1-[4-(3-Butoxy-2-hydroxy-propoxymethyl)-phenyl]-2-hydroxy-2-methyl-propan-1-one
[4-(4-Hydroxy-butoxymethyl)-phenyl]-(1-hydroxy-cyclohexyl)-methanone
2-Ethyl-2-hydroxy-1-(4-isopropoxymethyl-phenyl)-hexan-1-one
2-Ethoxy-1-(4-othoxymethyl-phenyl)-2-methyl-propan-1-one
2-Allyloxy-1-(4-methoxymethyl-phenyl)-2-methyl-propan-1-one
2-Hydroxy-2-methyl-1-(4-trimethylsilanyloxymethyl-phenyl)-propan-1-one
2-Methyl-2-trimethylsilanyloxy-1-(4-trimethylsilanyloxymethyl-phenyl)-propan-1-one
1-(4-Methoxymethyl-phenyl)-2-methyl-2-trimethylsilanyloxy-propan-1-one
2-Hydroxy-2-methyl-1-[3-(1,3,3,3-tetramethyl-1-[(trimethylsilyl)oxy]disiloxanyl)-propyloxymethyl-phenyl]-propan-1-one
2-Hydroxy-1-[4-(2-hydroxy-ethylsulfanylmethyl)-phenyl]-2-methyl-propan-1-one
Acetic acid 4-(2-hydroxy-2-methyl-propionyl)-benzyl ester
Benzoic acid 4-(2-hydroxy-2-methyl-propionyl)-benzyl ester
Butyric acid 4-(2-hydroxy-2-methyl-propionyl)-benzyl ester
Octadecanoic acid 4-(2-hydroxy-2-methyl-propionyl)-benzyl ester

EXAMPLES OF COMPOUNDS OF THE FORMULA II 1-(3,4-Bis-methoxymethyl-phenyl)-2-hydroxy-2-methyl-propan-1-one
1-(3,4-Bis-methoxymethyl-phenyl)-2-methyl-2-morpholin-4-yl-propan-1-one
(1-Hydroxy-cyclohexyl)-(4-hydroxymethyl-3-methyl-phenyl)-methanone
(1-Hydroxy-cyclohexyl)-(3-hydroxymethyl-4-methyl-phenyl)-methanone
{4-[4-(1-Hydroxy-cyclohexanecarbonyl)-2-methyl-benzyloxymethyl]-3-methyl-phenyl}-(1-hydroxy-cyclohexyl)-methanone
{3-[4-(1-Hydroxy-cyclohexanecarbonyl)-2-methyl-benzyloxymethyl]-4-methyl-phenyl}-(1-hydroxy-cyclohexyl)-methanone
{3-[5-(1-Hydroxy-cyclohexanecarbonyl)-2-methyl-benzyloxymethyl]-4-methyl-phenyl}-(1-hydroxy-cyclohexyl)-methanone
2-Hydroxy-1-{4-[4-(2-hydroxy-2-methyl-propionyl)-2-methyl-benzyoxymethyl]-3-methyl-phenyl}-2-methyl-propan-1-one
2-Hydroxy-1-{3-[4-(2-hydroxy-2-methyl-propionyl)-2-methyl-benzyloxymethyl]-4-methyl-phenyl}-2-methyl-propan-1-one
2-Hydroxy-1-{3-[5-(2-hydroxy-2-methyl-propionyl)-2-methyl-benzyloxymethyl]-4-methyl-phenyl}-2-methyl-propan-1-one
2-Hydroxy-1-{3-hydroxymethyl-4-[2-hydroxymethyl-4-(2-hydroxy-2-methyl-propionyl)-benzyloxymethyl]-phenyl}-2-methyl-propan-1-one
2-Hydroxy-1-{3-hydroxymethyl-4-[2-hydroxymethyl-5-(2-hydroxy-2-methyl-propionyl)-benzyloxymethyl]-phenyl}-2-methyl-propan-1-one
2-Hydroxy-1-{4-hydroxymethyl-3-[2-hydroxymethyl-5-(2-hydroxy-2-methyl-propionyl)-benzyloxymethyl]-phenyl}-2-methyl-propan-1-one
2-Hydroxy-1-{4-[4-(2-hydroxy-2-methyl-propionyl)-2-methoxymethyl-benzyloxymethyl]-3-methoxymethyl-phenyl}-2-methyl-propan-1-one
2-Hydroxy-1-{4-[5-(2-hydroxy-2-methyl-propionyl)-2-methoxymethyl-benzyloxymethyl]-3-methoxymethyl-phenyl}-2-methyl-propan-1-one 2-Hydroxy-1-{3-[4-(2-hydroxy-2-methyl-propionyl)-2-methoxymethyl-benzyloxymethyl]-4-methoxymethyl-phenyl}-2-methyl-propan-1-one 2-Hydroxy-1-{3-[5-(2-hydroxy-2-methyl-propionyl)-2-methoxymethyl-benzyloxymethyl]-4-methoxymethyl-phenyl}-2-methyl-propan-1-one 2-Hydroxy-1-[4-({[4-(2-hydroxy-2-methyl-propionyl)-2-methyl-benzyl]-methyl-amino}methyl)-3-methyl-phenyl]-2-methyl-propan-1-one 2-Hydroxy-1-[3-({[4-(2-hydroxy-2-methyl-propionyl)-2-methyl-benzyl]-methyl-amino}-methyl)-4-methyl-phenyl]-2-methyl-propan-1-one 2-Hydroxy-1-(3-{[5-(2-hydroxy-2-methyl-propionyl)-2-methyl-benzylamino]-methyl}-4-methyl-phenyl)-2-methyl-propan-1-one 2-Hydroxy-1-{4-[4-(1-hydroxy-cyclohexanecarbonyl)-2-methyl-benzyloxymethyl]-3-methyl-phenyl}-2-methyl-propan-1-one 2-Hydroxy-1-{4-[5-(1-hydroxy-cyclohexanecarbonyl)-2-methyl-benzyloxymethyl]-3-methyl-phenyl}-2-methyl-propan-1-one 2-Hydroxy-1-{3-[5-(1-hydroxy-cyclohexanecarbonyl)-2-methyl-benzyloxymethyl]-4-methyl-phenyl}-2-methyl-propan-1-one 1-[3,4-Bis-(1-methoxy-ethyl)-phenyl]-2-hydroxy-2-methyl-propan-1-one 1-[3-Ethyl-4-(1-methoxy-ethyl)-phenyl]-2-hydroxy-2-methyl-propan-1-one 1-[4-Ethyl-3-(1-methoxy-ethyl)-phenyl]-2-hydroxy-2-methyl-propan-1-one 1-(3,4-Bis-ethoxymethyl-phenyl)-2-hydroxy-2-methyl-propan-1-one 1-(4-Ethoxymethyl-3-methyl-phenyl)-2-hydroxy-2-methyl-propan-1-one 1-(3-Ethoxymethyl-4-methyl-phenyl)-2-hydroxy-2-methyl-propan-1-one 2-Hydroxy-1-(4-hydroxymethyl-3-methoxymethyl-phenyl)-2-methyl-propan-1-one 2-Hydroxy-1-(3-hydroxymethyl-4-methoxymethyl-phenyl)-2-methyl-propan-1-one 1-(3,4-Bis-hydroxymethyl-phenyl)-2-hydroxy-2-methyl-propan-1-one 1-(2,4-Bis-hydroxymethyl-phenyl)-2-hydroxy-2-methyl-propan-1-one 1-(2,4-Bis-methoxymethyl-phenyl)-2-hydroxy-2-methyl-propan-1-one 2-Hydroxy-1-(4-hydroxymethyl-3-methyl-phenyl)-2-methyl-propan-1-one 2-Hydroxy-1-(3-hydroxymethyl-4-methyl-phenyl)-2-methyl-propan-1-one 2-Hydroxy-1-[4-(1-hydroxy-ethyl)-3-methyl-phenyl]-2-methyl-propan-1-one 1-(3-Ethyl-4-hydroxymethyl-phenyl)-2-hydroxy-2-methyl-propan-1-one 2-Hydroxy-1-[3-(1-hydroxy-ethyl)-4-methyl-phenyl]-2-methyl-propan-1-one 2-Hydroxy-1-(3-hydroxymethyl-4-methyl-phenyl)-2-methyl-propan-1-one 1-(3-Dimethylaminomethyl-4-hydroxymethyl-phenyl)-2-hydroxy-2-methyl-propan-1-one 1-(3-Dimethylaminomethyl-4-methoxymethyl-phenyl)-2-hydroxy-2-methyl-propan-1-one 1-(4-Dimethylaminomethyl-3-hydroxymethyl-phenyl)-2-hydroxy-2-methyl-propan-1-one 1-(4-Dimethylaminomethyl-3-methoxymethyl-phenyl)-2-hydroxy-2-methyl-propan-1-one 1-(3,4-Bis-dimethylaminomethyl-phenyl)-2-hydroxy-2-methyl-propan-1-one 1-(4-Dimethylaminomethyl-3-morpholin-4-ylmethyl-phenyl)-2-hydroxy-2-methyl-propan-1-one 1-(3,4-Bis-morpholin-4-ylmethyl-phenyl)-2-hydroxy-2-methyl-propan-1-one 2-Hydroxy-1-(4-hydroxymethyl-3-morpholin-4-ylmethyl-phenyl)-2-methyl-propan-1-one 2-Hydroxy-(3-methoxy methyl-4-morpholin-4-ylmethyl-phenyl)-2-methyl-propan-1-one

EXAMPLES OF COMPOUNDS OF THE FORMULA III

{6-[4-(2-Hydroxy-2-methyl-propionyl)-benzyloxycarbonylamino]-hexyl}-carbamic acid 4-(2-hydroxy-2-methyl-propionyl)-benzyl ester {4-[4-(2-Hydroxy-2-methyl-propionyl)-benzyloxycarbonylamino]-butyl}-carbamic acid 4-(2-hydroxy-2-methyl-propionyl)-benzyl ester {9-[4-(2-Hydroxy-2-methyl-propionyl)-benzyloxycarbonylamino]-nonyl}-carbamic acid 4-(2-hydroxy-2-methyl-propionyl)-benzyl ester {12-[4-(2-Hydroxy-2-methyl-propionyl)-benzyloxycarbonylamino]-dodecyl}-carbamic acid 4-(2-hydroxy-2-methyl-propionyl)-benzyl ester {18-[4-(2-Hydroxy-2-methyl-propionyl)-benzyloxycarbonylamino]-octadecyl}-carbamic acid 4-(2-hydroxy-2-methyl-propionyl)-benzyl ester {6-[4-(2-Hydroxy-2-methyl-propionyl)-benzyloxycarbonylamino]-2,4,4-trimethyl-hexyl}-carbamic acid 4-(2-hydroxy-2-methyl-propionyl)-benzyl ester {6-[4-(2-Hydroxy-2-methyl-propionyl)-benzyloxycarbonylamino]-2,2,4-trimethyl-hexyl}-carbamic acid 4-(2-hydroxy-2-methyl-propionyl)-benzyl ester (3-{[4-(2-Hydroxy-2-methyl-propionyl)-benzyloxycarbonylamino]-methyl}-3,5,5-trimethyl-cyclohexyl)-carbamic acid 4-(2-hydroxy-2-methyl-propionyl)-benzyl ester (3-{[4-(2-Hydroxy-2-methyl-propionyl)-benzyloxycarbonylamino]-methyl}-cyclohexylmethyl)-carbamic acid 4-(2-hydroxy-2-methyl-propionyl)-benzyl ester (3-{[4-(2-Hydroxy-2-methyl-propionyl)-benzyloxycarbonylamino]-methyl}-benzyl)-carbamic acid 4-(2-hydroxy-2-methyl-propionyl)-benzyl ester (4-{4-[4-(2-Hydroxy-2-methyl-propionyl)-benzyloxycarbonylamino]-cyclohexyl methyl}cyclohexyl)-carbamic acid 4-(2-hydroxy-2-methyl-propionyl)-benzyl ester (4-{4-[4-(2-Hydroxy-2-methyl-propionyl)-benzyloxycarbonylamino]-3-methyl-cyclohexylmethyl}-2-methyl-cyclohexyl)-carbamic acid 4-(2-hydroxy-2-methyl-propionyl)-benzyl ester (4-{4-[4-(2-Hydroxy-2-methyl-propionyl)-benzyloxycarbonylamino]-benzyl}-phenyl)-carbamic acid 4-(2-hydroxy-2-methyl-propionyl)-benzyl ester

[4-(1-{4-[4-(2-Hydroxy-2-methyl-propionyl)-benzyloxycarbonylamino]-3-methyl-phenyl}methyl)-2-methyl-phenyl]-carbamic acid 4-(2-hydroxy-2-methyl-propionyl)-benzyl ester (4-{4-[4-(2-Hydroxy-2-methyl-propionyl)-benzyloxycarbonylamino]-phenoxy}phenyl)-carbamic acid 4-(2-hydroxy-2-methyl-propionyl)-benzyl ester

[1-(3-{1-[4-(2-Hydroxy-2-methyl-propionyl)-benzyloxycarbonylamino]-1-methyl-ethyl}-phenyl)-1-methyl-ethyl]-carbamic acid 4-(2-hydroxy-2-methyl-propionyl)-benzyl ester {4-[4-(2-Hydroxy-2-methyl-propionyl)-benzyloxycarbonylamino]-phenyl}-carbamic acid 4-(2-hydroxy-2-methyl-propionyl)-benzyl ester {3-[4-(2-Hydroxy-2-methyl-propionyl)-benzyloxycarbonylamino]-4-methyl-phenyl}-carbamic acid 4-(2-hydroxy-2-methyl-propionyl)-benzyl ester (3-[4-(2-Hydroxy-2-methyl-propionyl)-benzyloxycarbonylamino]-4-methyl-cyclohexyl)-carbamic acid 4-(2-hydroxy-2-methyl-propionyl)-benzyl ester {6-[4-(2-Hydroxy-2-methyl-propionyl)-benzyloxycarbonylamino]-bicyclo[2.2.1]hept-2-yl}-carbamic acid 4-(2-hydroxy-2-methyl-propionyl)-benzyl ester {5-[4-(2-Hydroxy-2-methyl-propionyl)-benzyloxycarbonylamino]-bicyclo[2.2.1]hept-2-yl}-carbamic acid 4-(2-hydroxy-2-methyl-propionyl)-benzyl ester {6-[3-{6-[4-(2-Hydroxy-2-methyl-propionyl)-benzyloxycarbonylamino]-hexyl}-5-(6-isocyanatohexyl)-2,4,6-trioxo-[1,3,5]triazinan-1-yl]-hexyl}-carbamic acid 4-(2-hydroxy-2-methyl-propionyl)-benzyl ester

[6-(3-{6-[4-(2-Hydroxy-2-methyl-propionyl)-benzyloxycarbonylamino]-hexyl}-2,4-dioxo-[1,3]diazetidin-1-yl)-hexyl]-carbamic acid 4-(2-hydroxy-2-methyl-propionyl)-benzyl ester 2-Hydroxy-1-(4-{2-[4-(2-hydroxy-2-methyl-propionyl)-benzyloxy]-ethoxymethyl}-phenyl)-2-methyl-propan-1-one 2-Hydroxy-1-(4-{3-[4-(2-hydroxy-2-methyl-propionyl)-benzyloxy]-propoxymethyl}phenyl)-2-methyl-propan-1-one 2-Hydroxy-1-(4-{4-[4-(2-hydroxy-2-methyl-propionyl)-benzyloxy]-butoxymethyl}-phenyl)-2-methyl-propan-1-one 2-Hydroxy-1-(4-{6-[4-(2-hydroxy-2-methyl-propionyl)-benzyloxy]-hexyloxymethyl}-phenyl)-2-methyl-propan-1-one 2-Hydroxy-1-(4-{10-[4-(2-hydroxy-2-methyl-propionyl)-benzyloxy]-decyloxymethyl}-phenyl)-2-methyl-propan-1-one 2-Hydroxy-1-(4-{12-[4-(2-hydroxy-2-methyl-propionyl)-benzyloxy]-dodecyloxymethyl}-phenyl)-2-methyl-propan-1-one 2-Hydroxy-1-(4-{18-[4-(2-hydroxy-2-methyl-propionyl)-benzyloxy]-octadecyloxymethyl}-phenyl)-2-methyl-propan-1-one 2-Hydroxy-1-(4-{4-[4-(2-hydroxy-2-methyl-propionyl)-benzyloxy]-1,3-dimethyl-butoxymethyl}phenyl)-2-methyl-propan-1-one 2-Hydroxy-1-(4-{6-[4-(2-hydroxy-2-methyl-propionyl)-benzyloxy]-2,4-dimethyl-heptyloxymethyl}-phenyl)-2-methyl-propan-1-one 2-Hydroxy-1-(4-{2-hydroxy-3-[4-(2-hydroxy-2-methyl-propionyl)-benzyloxy]-propoxymethyl}-phenyl)-2-methyl-propan-1-one 2-Hydroxy-1-[4-(2-{2-[4-(2-hydroxy-2-methyl-propionyl)-benzyloxy]-ethoxy}-ethoxymethyl)-phenyl]-2-methyl-propan-1-one 2-Hydroxy-1-{4-[2-(2-{2-[4-(2-hydroxy-2-methyl-propionyl)-benzyloxy]-ethoxy}-ethoxy)-ethoxymethyl]-phenyl}-2-methyl-propan-1-one 2-Hydroxy-1-(4-{2-[2-(2-{2-[4-(2-hydroxy-2-methyl-propionyl)-benzyloxy]-ethoxy}ethoxy)-ethoxy]-ethoxymethyl}-phenyl)-2-methyl-propan-1-one 2-Hydroxy-1-[{4-(2-{2-[2-(2-{2-[4-(2-hydroxy-2-methyl-propionyl)-benzyloxy]-ethoxy}-ethoxy)-ethoxy]-ethoxy)ethoxymethyl}-phenyl]-2-methyl-propan-1-one 2-Hydroxy-1-{4-[2-(2-{2-[2-(2-[4-(2-hydroxy-2-methyl-propionyl)-benzyloxy]-ethoxy}-ethoxy)-ethoxy]-ethoxy}ethoxy)-ethoxymethyl]-phenyl}-2-methyl-propan-1-one 2-Hydroxy-1-(4-(2-[2-(2-{2-[2-(2-{2-[4-(2-hydroxy-2-methyl-propionyl)-benzyloxy]-ethoxy}-ethoxy)-ethoxy]-ethoxy-ethoxy)-ethoxy]-ethoxymethyl}-phenyl)-2-methyl-propan-1-one 2-Hydroxy-1-[4-(2-{2-[4-(2-hydroxy-2-methyl-propionyl)-benzyloxy]-propoxy}-methyl-ethoxymethyl)-phenyl]-2-methyl-propan-1-one 2-Hydroxy-1-[4-(2-{2-[4-(2-hydroxy-2-methyl-propionyl)-benzyloxy]-propoxy}propoxymethyl)-phenyl]-2-methyl-propan-1-one 2-Hydroxy-1-{4-[2-(2-{2-[4-(2-hydroxy-2-methyl-propionyl)-benzyloxy]-propoxy}propoxy)-propoxymethyl]-phenyl}-2-methyl-propan-1-one 2-Hydroxy-1-{4-[2-(2-{2-[4-(2-hydroxy-2-methyl-propionyl)-benzyloxy]-propoxy}-1-methyl-ethoxy)-1-methyl-ethoxymethyl]-phenyl}-2-methyl-propan-1-one 2-Hydroxy-1-(4-{4-[4-(2-hydroxy-2-methyl-propionyl)-benzyloxymethyl]-cyclohexylmethoxymethyl}-phenyl)-2-methyl-propan-1-one 2-Hydroxy-1-(4-{4-[4-(2-hydroxy-2-methyl-propionyl)-benzyloxymethyl]-benzyloxymethyl}-phenyl)-2-methyl-propan-1-one 2-Hydroxy-1-(4-{4-[4-(2-hydroxy-2-methyl-propionyl)-benzyloxy]-cyclohexyloxymethyl}phenyl)-2-methyl-propan-1-one 2-Hydroxy-1-[4-(2-{4-[1-(4-{2-[4-(2-hydroxy-2-methyl-propionyl)-benzyloxy]-ethoxy}phenyl)-1-methyl-ethyl]-phenoxy}ethoxymethyl)-phenyl]-2-methyl-propan-1-one 2-Hydroxy-1-[4-(2-{4-[1-(4-{2-[4-(2-hydroxy-2-methyl-propionyl)-benzyloxy]-ethoxy}-cyclohexyl)-1-methyl-ethyl]-cyclohexyloxy}ethoxymethyl)-cyclohexyl]-2-methyl-propan-1-one 2-Hydroxy-1-{4-[2-({2-[4-(2-hydroxy-2-methyl-propionyl)-benzyloxy]-ethyl}-methyl-amino)-ethoxymethyl]-phenyl}-2-methyl-propan-1-one 2-Hydroxy-1-{4-[2-((2-hydroxy-ethyl)-{2-[4-(2-hydroxy-2-methyl-propionyl)-benzyloxy]-ethyl}amino)-ethoxymethyl]-phenyl}-2-methyl-propan-1-one 2-Hydroxy-1-(4-{2-hydroxymethyl-2-[4-(2-hydroxy-2-methyl-propionyl)-benzyloxymethyl]-butoxymethyl}-phenyl)-2-methyl-propan-1-one 2-Hydroxy-1-(4-{3-hydroxy-2-hydroxymethyl-2-[4-(2-hydroxy-2-methyl-propionyl)-benzyloxymethyl]-propoxymethyl}-phenyl)-2-methyl-propan-1-one 1-(4-{3-Ethyl-3-(2-hydroxy-ethyl)-5-[4-(2-hydroxy-2-methyl-propionyl)-benzyloxy]-pentyloxymethyl}-phenyl)-2-hydroxy-2-methyl-propan-1-one 1-(4-{3,3-Bis-(2-hydroxy-ethyl)-5-[4-(2-hydroxy-2-methyl-propionyl)-benzyoxy]-pentyloxymethyl}-phenyl)-2-hydroxy-2-methyl-propan-1-one 1-(2-Hydroxy-ethyl)-3,5-bis-{2-[4-(2-hydroxy-2-methyl-propionyl)-benzyloxy]-ethyl}-[1,3,5]triazinane-2,4,6-trione 2-Hydroxy-1-{4-[2-((2-hydroxy-ethyl)-{2-[4-(2-hydroxy-2-methyl-propionyl)-benzyloxy]-ethyl}-phosphonyl)-ethoxymethyl]-phenyl}-2-methyl-propan-1-one 2-Hydroxy-1-{4-[2-((2-hydroxy-ethyl)-{2-[4-(2-hydroxy-2-methyl-propionyl)-benzyloxy]-ethyl}-phosphinoyl)-ethoxymethyl]-phenyl}-2-methyl-propan-1-one 1-{4-[2-(Bis-{2-[4-(2-hydroxy-2-methyl-propionyl)-benzyloxy]-ethyl}-phosphanyl)-ethoxymethyl]-phenyl}-2-hydroxy-2-methyl-propan-1-one 1-(4-[2-(Bis-{2-[4-(2-hydroxy-2-methyl-propionyl)-benzyloxy]-ethyl}phosphinoyl)-ethoxymethyl]-phenyl}-2-hydroxy-2-methyl-propan-1-one 2-Hydroxy-1-{4-[3-({3-[4-(2-hydroxy-2-methyl-propionyl)-benzyloxy]-propyl}-dimethyl-silanyl)-propoxymethyl]-phenyl}-2-methyl-propan-1-one 2-Hydroxy-1-{4-[2-({2-[4-(2-hydroxy-2-methyl-propionyl)-benzyloxy]-ethoxy}dimethyl-silanyloxy)-ethoxymethyl]-phenyl}-2-methyl-propan-1-one 1-{4-[3-(Bis-{3-[4-(2-hydroxy-2-methyl-propionyl)-benzyloxy]-propyl}methyl-silanyl)-propoxymethyl]-phenyl}-2-hydroxy-2-methyl-propan-1-one 1-{4-[3-(Bis-{3-[4-(2-hydroxy-2-methyl-propionyl)-benzyloxy]-ethoxy}-methyl-silanyloxy)-ethoxymethyl]-phenyl}-2-hydroxy-2-methyl-propan-1-one Oxalic acid bis-[4-(2-hydroxy-2-methyl-propionyl)-benzyl] ester Malonic acid bis-[4-(2-hydroxy-2-methyl-propionyl)-benzyl]ester Succinic acid bis-[4-(2-hydroxy-2-methyl-propionyl)-benzyl]ester Pentanedioic acid bis-[4-(2-hydroxy-2-methyl-propionyl)-benzyl]ester Hexanedioic acid bis-[4-(2-hydroxy-2-methyl-propionyl)-benzyl]ester Decanedioic acid bis-[4-(2-hydroxy-2-methyl-propionyl)-benzyl]ester Tetradecanedioic acid bis-[4-(2-hydroxy-2-methyl-propionyl)-benzyl]ester

[4-(2-Hydroxy-2-methyl-propionyl)-benzyloxycarbonylmethoxy]-acetic acid 4-(2-hydroxy-2-methyl-propionyl)-benzyl ester Terephthalic acid bis-[4-(2-hydroxy-2-methyl-propionyl)-benzyl]ester Isophthalic acid bis-[4-(2-hydroxy-2-methyl-propionyl)-benzyl]ester Phthalic acid bis-[4-(2-hydroxy-2-methyl-propionyl)-benzyl]ester Cyclohexane-1,2-dicarboxylic acid bis-[4-(2-hydroxy-2-methyl-propionyl)-benzyl]ester Cyclohexane-1,3-dicarboxylic acid bis-[4-(2-hydroxy-2-methyl-propionyl)-benzyl]ester Cyclohexane-1,4-dicarboxylic acid bis-[4-(2-hydroxy-2-methyl-propionyl)-benzyl]ester Benzene-1,3,5-tricarboxylic acid tris-[4-(2-hydroxy-2-methyl-propionyl)-benzyl]ester Benzene-1,2,4-tricarboxylic acid tris-[4-(2-hydroxy-2-methyl-propionyl)-benzyl]ester Benzene-1,2,4,5-tetracarboxylic acid tetrakis-[4-(2-hydroxy-2-methyl-propionyl)-benzyl]ester 3,4-Bis-[4-(2-hydroxy-2-methyl-propionyl)-benzyloxycarbonyl]-hexanedioic acid bis-[4-(2-hydroxy-2-methyl-propionyl)-benzyl]ester

EXAMPLES OF COMPOUNDS OF THE FORMULA IV 1-(1,3-Dihydro-isobenzofuran-5-yl)-2-hydroxy-2-methyl-propan-1-one (1,3-Dihydro-isobenzofuran-5-yl)-(1-hydroxy-cyclohexyl)-methanone 1-(2,3-Dihydro-1H-isoindol-5-yl)-2-hydroxy-2-methyl-propan-1-one 2-Hydroxy-2-methyl-1-(2-methyl-2,3-dihydro-1H-isoindol-5-yl)-propan-1-one 1-(1,3-Dihydro-isobenzofuran-5-yl)-2-methyl-2-morpholin-4-yl-propan-1-one 1-(1,3-Dimethyl-1,3-dihydro-isobenzofuran-5-yl)-2-hydroxy-2-methyl-propan-1-one

EXAMPLES OF COMPOUNDS OF THE FORMULA V 1-(5,8-Dihydroxy-5,6,7,8-tetrahydro-naphthalen-2-yl)-2-hydroxy-2-methyl-propan-1-one 1-(5,8-Bis-dimethylamino-5,6,7,8-tetrahydro-naphthalen-2-yl)-2-dimethylamino-2-methyl-propan-1-one 1-(5,8-Dimethoxy-5,6,7,8-tetrahydro-naphthalen-2-yl)-2-hydroxy-2-methyl-propan-1-one 1-(5,9-Dihydroxy-6,7,8,9-tetrahydro-5H-benzocyclohepten-2-yl)-2-hydroxy-2-methyl-propan-1-one

EXAMPLES OF COMPOUNDS OF THE FORMULA VI

2-Hydroxy-2-methyl-1-(11-oxa-tricyclo[6.2.1.0$^{2,7}$]undeca-2(7),3,5-trien-4-yl)-propan-1-one (1-Hydroxy-cyclohexyl)-(11-oxa-tricyclo[6.2.1.0$^{2,7}$]undeca-2(7),3,5-trien-4-yl)-methanone 2-Hydroxy-2-methyl-1-(9-methyl-1,2,3,4-tetrahydro-1,4-epiazano-naphthalen-6-yl)-propan-1-one 2-Hydroxy-2-methyl-1-(12-oxa-tricyclo[6.3.1.0$^{2,7}$]dodeca-2(7),3,5-trien-4-yl)-propan-1-one 2-Hydroxy-2-methyl-1-(12-methyl-12-aza-tricyclo[6.3.1.0$^2$ 7]dodeca-2(7),3,5-trien-4-yl)-propan-1-one Preparation of the Compounds:

Preparation of compounds I, II, III, IV, V and VI is performed by a) reaction of an alkylated aromatic compound Ar—CHR$_3$R$_4$ or dialkylated aromatic compound R$_5$R$_6$HC—Ar—CHR$_3$R$_4$ or benzocycloalkane with an acid halide of formula R$_1$R$_2$CH—COHal in the presence of a Friedel-Crafts catalyst, whereupon a compound of formula A, B or C is obtained,

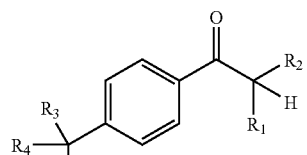

A

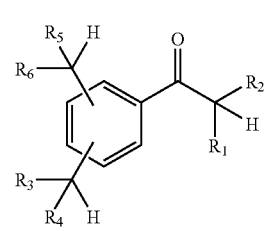

B

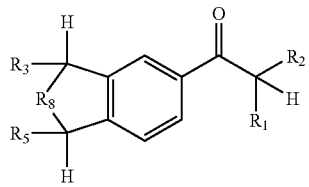

C b) halogenation of an aromatic ketone of formula A, B or C, and subsequent bromination and hydrolysis, whereupon a compound of formula D, E, F, G or H is obtained,

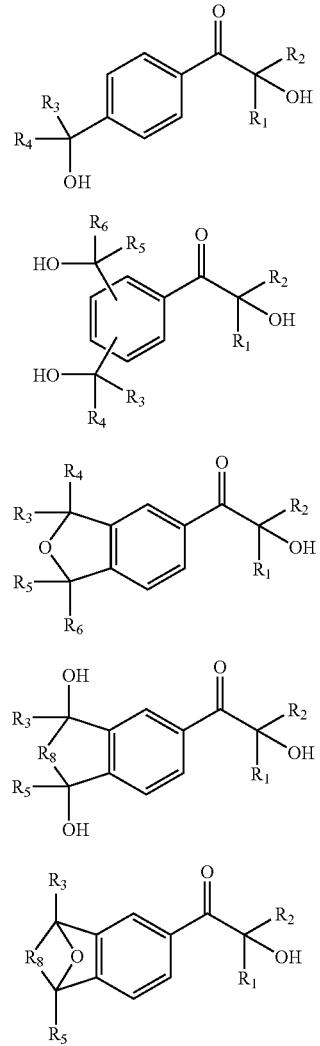

c) optionally, selective replacement of the benzylic hydroxy group of a compound of formula D, E or G by reaction
with an alcohol in the presence of an acid as catalyst for the preparation of an ether,
with a carboxylic acid for the preparation of an ester,
with an isocyanate for the preparation of a urethane,
with a diol, dicarboxylic acid or diisocyanate for the preparation of a bridged compound,
with a siloxane for the preparation of a silicone derivative,
d) optionally, reaction of the alpha-hydroxy group in the resulting compound of formula D, E, F, G, H or a subsequent product thereof,
e) optionally, separation of a resulting mixture,
or
f) reaction of an alkylated aromatic compound Ar—CHR$_3$R$_4$ or dialkylated aromatic compound R$_5$R$_6$HC—Ar—CHR$_3$R$_4$ or benzocycloalkane with an acid halide of formula R$_1$R$_2$CH—COHal in the presence of a Friedel-Crafts catalyst, whereupon a compound of formula A, B or C is obtained,

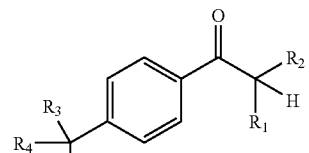
A

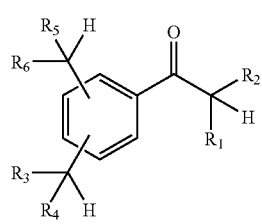
B

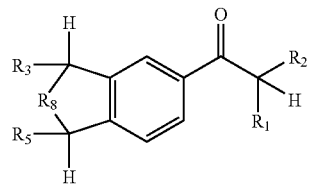
C g) halogenation of an aromatic ketone of formula A, B or C, and subsequent bromination and aminolysis, whereupon a compound of formula I, K, L, M or N is obtained,

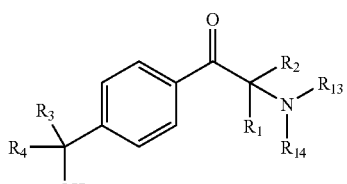
I

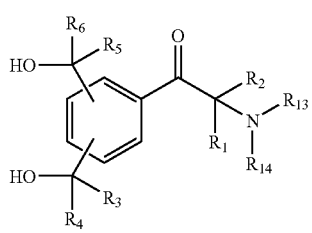
K

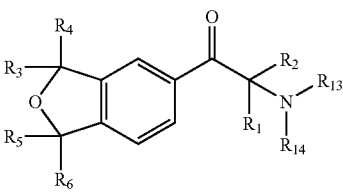
L

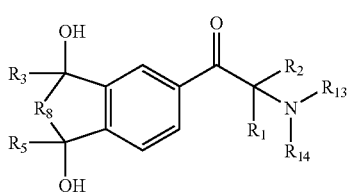
M

-continued

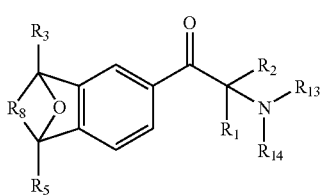

h) optionally, selective replacement of the benzylic hydroxy group of a compound of formula I, K or M by reaction
with an alcohol in the presence of an acid as catalyst for the preparation of an ether,
with a carboxylic acid for the preparation of an ester,
with an isocyanate for the preparation of a urethane,
with a diol, dicarboxylic acid or diisocyanate for the preparation of a bridged compound,
with a siloxane for the preparation of a silicone derivative,
i) optionally, separation of a resulting mixture.

The preparation of the ketone is carried out by Friedel-Crafts acylation, wherein the alkylated or dialkylated aromatic compound, e.g. toluene or xylene, is reacted in the presence of a Lewis acid, for example with isobutyryl halide. The known Friedel-Crafts catalysts are suitable, for example aluminium chloride, aluminium bromide, zinc chloride, tin chloride, iron(III) chloride, bismuth chloride or boron trifluoride. Aluminium chloride is preferred.

In the present Friedel-Crafts reaction, it is possible to bring the aromatic compound and the catalyst together first and to add the acid halide thereto, as described in German Application DE 30 08 411 A1 (1980) of Merck.

It is, however, also possible to bring the aromatic compound and the acid halide together first and to add the catalyst.

Acylation can be carried out in the presence of a solvent. Suitable solvents are any solvents that are inert under the indicated reaction conditions, for example ethylene chloride, trichloroethylene, methylene chloride, tetrachloroethane, chlorobenzene, bromobenzene, dichlorobenzene, cyclohexane, methylcyclohexane, carbon disulfide, nitromethane, nitroethane, nitropropane and nitrobenzene. Preference is given to the reaction component also being the solvent, for example toluene, 1,2-xylene, ethylbenzene or Tetralin.

The reaction temperature is from −20° C. to 20° C., preferably from 0° C. to 10° C., especially from 0° C. to 5° C.

For the reaction there is used an excess of aluminium chloride, relative to acid halide, of from 1.0 to 1.2 equivalents, preferably from 1.0 to 1.1 equivalents, especially from 1.0 to 1.05 equivalents. The excess of aluminium chloride should be at least as large as any excess of acid halide.

Without being isolated, the crude ketone of step (a) can be directly subjected, in step (b), to halogenation (preferably bromination) of the keto group and subsequent bromination of the alkyl group. Bromination may also be carried out by means of free radicals, with light acting as free-radical-former. It is, however, also possible to use customary free-radical-formers such as dibenzoyl peroxide or azoisobutyronitrile.

Subsequent hydrolysis with aqueous alkali metal hydroxide yields the crude product (compound D, E, F, G or H), dissolved in the organic phase.

The benzylic hydroxy group is capable of being replaced and can be reacted selectively, for example,
with an alcohol in the presence of an acid as catalyst for the preparation of an ether,
with a carboxylic acid for the preparation of an ester,
with an isocyanate for the preparation of a urethane,
with a siloxane for the preparation of a silicone derivative,
with a diol, dicarboxylic acid or diisocyanate for the preparation of a bridged compound; suitable diols, diisocyanates, dicarboxylic acids and siloxanes are indicated in the above list.

The reaction of alpha-hydroxy groups can, where applicable, be carried out in accordance with known methods such as those described in, for example, EP-A 003 002, EP 138 754 B1 or U.S. Pat. No. 5,977,357.

The compounds of formula I, II, III, IV, V or VI and mixtures thereof are suitable photoinitiators.

The invention accordingly also provides a photocurable composition comprising
(A) at least one ethylenically unsaturated free-radically photopolymerizable compound; and
(B) at least one photoinitiator of the formula I, II, II, III, IV, V or VI and mixtures thereof;
(C) optionally thermally crosslinkable compounds;
(D) optionally further additives;
(E) optionally further photoinitiators.

The invention further provides a process for producing coatings having scratch-resistant and/or chemical resistant surfaces, in which a photocurable composition as defined above is applied to a substrate; and is cured either only by exposure to electromagnetic radiation with a wavelength ranging from 200 nm into the NIR (near infrared) region or IR region, or by exposure to electromagnetic radiation with a wavelength ranging from 200 nm into the NIR region or IR region and prior, simultaneous and/or subsequent exposure to heat.

NIR-curing

The NIR radiation used in the process according to the invention is short-wave infrared radiation in the wavelength range from about 750 nm to about 1 500 nm, preferably 750 nm to 1200 nm. Radiation sources for NIR radiation include, for example, conventional NIR radiation emitters, which are available commercially (for example, from Adphos).

IR-curing

The IR radiation used in the process according to the invention is medium wave radiation in the wavelength range from about 1500 nm to about 3000 nm and/or longer-wavelength infrared radiation in the wavelength range above 3000 nm.

IR radiation emitters of this kind are available commercially (for example, from Heraeus).

UV-curing

The photochemical curing step is carried out usually using light of wavelengths from about 200 nm to about 600 nm, especially from 200 to 450 nm. As light sources there are used a large number of the most varied types. Both point sources and planiform projectors (lamp carpets) are suitable. Examples are: carbon arc lamps, xenon arc lamps, medium-, high- and low-pressure mercury lamps, optionally doped with metal halides (metal halide lamps), LED-lamps, microwave-excited metal-vapor lamps, excimer lamps, super actinic fluorescent tubes, fluorescent lamps, argon filament lamps, electronic flash lamps, photographic flood lights, electron beams and X-rays generated by means of synchrotrons or laser plasma or microwave plasma.

The inventive photoinitiators of the formula I to VI can be used in purely photocurable formulations or in photochemically and thermally curable formulations. Thermal curing may take place before, during or after exposure to light.

The invention accordingly also provides a process as described above in which the photocurable formulation comprises as a further component at least one thermally crosslinkable compound (C) and the formulation is cured by exposure to light whose wavelength extends from 200 nm into the NIR region or IR region and by prior, simultaneous and/or subsequent exposure to heat.

Definition of the Ethylenically Unsaturated Compound A

Suitable compounds with olefinic double bonds are all the compounds that can be crosslinked by free radical polymerization of the double bond. The ethylenically unsaturated compound may be a monomer, an oligomer or a prepolymer, a mixture thereof or a copolymer thereof.

Monomers suitable for free-radical polymerization are, for example, ethylenically unsaturated polymerizable monomers selected from the group consisting of (meth)acrylates, alkenes, conjugated dienes, styrenes, acrolein, vinyl acetate, vinylpyrrolidone, vinylimidazole, maleic anhydride, fumaric anhydride, (meth)acrylic acid, (meth)acrylic acid derivatives such as esters and amides, vinyl halides and vinylidene halides. Preferred are compounds having (meth)acryloyl, vinyl and/or maleate groups. Especially preferred are (meth) acrylates.

Compounds which contain free-radically polymerizable double bonds in the form of the preferred (meth)acryloyl groups may be produced in accordance with conventional methods. This may proceed, for example, by: transesterifying OH-functional resins, such as OH-functional polyesters, polyacrylates, polyurethanes, polyethers or epoxy resins, with alkyl esters of (meth)acrylic acid; esterifying the stated OH-functional resins with (meth)acrylic acid; reacting the stated OH-functional resins with isocyanate-functional (meth)acrylates; reacting acid-functional resins, such as polyesters, polyacrylates, polyurethanes with epoxy-functional (meth)acrylates; reacting epoxy-functional resins, such as polyesters, poly-acrylates, epoxy resins with (meth)acrylic acid. These production methods stated by way of example are described in the literature and known to the person skilled in the art.

Examples of prepolymers or oligomers include (meth) acryloyl-functional (meth)acrylic copolymers, polyurethane (meth)acrylates, polyester (meth)acrylates, unsaturated polyesters, polyether (meth)acrylates, silicone (meth)acrylates and epoxy resin (meth)acrylates having number-average molecular masses from, for example, 500 to 10,000, preferably 500 to 5,000.

The (meth)acryloyl-functional prepolymers may be used in combination with reactive diluents, i.e. free-radically polymerizable low molecular weight compounds with a molar mass of below 500 g/mol. The reactive diluents may be mono-, di- or polyunsaturated. Examples of monounsaturated reactive diluents are (meth)acrylic acid and the esters thereof, maleic acid and the esters thereof, vinyl acetate, vinyl ether, substituted vinyl ureas, styrene, vinyltoluene. Examples of diunsaturated reactive diluents are di(meth) acrylates such as alkylene glycol di(meth)acrylate, polyethylene glycol di(meth)acrylate, 1,3-butanediol di-(meth)acrylate, vinyl(meth)acrylate, allyl(meth)acrylate, divinylbenzene, dipropylene glycol di(meth)acrylate, hexanediol di(meth)acrylate. Examples of polyunsaturated reactive diluents are glycerol tri(meth)acrylate, trimethylolpropane tri(meth)acrylate, pentaerythritol tri(meth)-acrylate, pentaerythritol tetra(meth)acrylate. The reactive diluents may be used alone or in admixture.

Suitable salts of acrylic acid or methacrylic acid are, for example, $(C_1\text{-}C_4\text{alkyl})_4$ammonium or $(C_1\text{-}C_4\text{alkyl})_3$NH salts, e.g. the tetramethylammonium, tetraethylammonium, trimethylammonium or triethylammonium salt, the trimethyl-2-hydroxyethylammonium or triethyl-2-hydroxyethylammonium salt, the dimethyl-2-hydroxyethylammonium or diethyl-2-hydroxyethylammonium salt.

The ethylenically unsaturated compounds may contain, in addition to the olefinic double bonds, one or more further, identical or different functional groups. Examples of functional groups include hydroxyl, isocyanate (optionally blocked), N-methylol, N-methylolether, ester, carbamate, epoxy, amino (optionally blocked), acetoacetyl, alkoxysilyl and carboxyl groups. Examples are polyurethane resins with (meth)acryloyl groups and glycerol mono- and di-(meth) acrylate, trimethylol propane mono- and di-(meth)acrylate or pentaerythritol tri(meth)-acrylate.

Thermally crosslinkable compounds are:

1. surface coatings based on cold- or hot-crosslinkable alkyd, acrylate, polyester, epoxy or melamine resins or mixtures of such resins, optionally with the addition of a curing catalyst;
2. two-component polyurethane surface coatings based on hydroxyl-group-containing acrylate, polyester or polyether resins and aliphatic or aromatic isocyanates, isocyanurates or polyisocyanates;
3. two-component polyurethane surface coatings based on thiol-group-containing acrylate, polyester or polyether resins and aliphatic or aromatic isocyanates, isocyanurates or polyisocyanates;
4. one-component polyurethane surface coatings based on blocked isocyanates, isocyanurates or polyisocyanates which are deblocked during stoving; the addition of melamine resins is also possible, if desired;
5. one-component polyurethane surface coatings based on aliphatic or aromatic urethanes or polyurethanes and hydroxyl-group-containing acrylate, polyester or polyether resins;
6. one-component polyurethane surface coatings based on aliphatic or aromatic urethane acrylates or polyurethane acrylates having free amine groups in the urethane structure and melamine resins or polyether resins, optionally with the addition of a curing catalyst;
7. two-component surface coatings based on (poly)ketimines and aliphatic or aromatic isocyanates, isocyanurates or polyisocyanates;
8. two-component surface coatings based on (poly)ketimines and an unsaturated acrylate resin or a polyacetoacetate resin or a methacrylamidoglycolate methyl ester;
9. two-component surface coatings based on carboxyl- or amino-group-containing polyacrylates and polyepoxides;
10. two-component surface coatings based on anhydride-group-containing acrylate resins and a polyhydroxy or polyamino component;
11. two-component surface coatings based on acrylate-containing anhydrides and polyepoxides;
12. two-component surface coatings based on (poly)oxazolines and anhydride-group-containing acrylate resins or unsaturated acrylate resins or aliphatic or aromatic isocyanates, isocyanurates or polyisocyanates;
13. two-component surface coatings based on unsaturated (poly)acrylates and (poly)-malonates;
14. thermoplastic polyacrylate surface coatings based on thermoplastic acrylate resins or extrinsically crosslinking acrylate resins in combination with etherified melamine resins;

15. surface-coating systems, especially clearcoats, based on malonate-blocked isocyanates with melamine resins (e.g. hexamethoxymethylmelamine) as crosslinkers (acid-catalysed);
16. UV-curable systems based on oligomeric urethane acrylates and/or acylate acrylates, optionally with the addition of other oligomers or monomers;
17. dual-cure systems, which are cured first thermally and then by UV, or vice versa, the constituents of the surface-coating formulation containing double bonds that can be caused to react by UV light and photoinitiators and/or by electron-beam curing.

Additives D

The above-described compositions may further comprise customary additives, which may, as an alternative, also be added after the polymerization. Such additives can be added in small amounts, e.g. UV-absorbers or light stabilizers, e.g. compounds selected from the group consisting of hydroxyphenylbenzotriazoles, hydroxyphenylbenzophenones, oxalamides and hydroxyphenyl-s-triazines. Particularly suitable light stabilizers are those selected from the group consisting of N-alkoxy-Hals compounds such as Tinuvin 123, or of sterically hindered amine-Hals compounds of the 2-(2-hydroxyphenyl)-1,3,5-triazine or 2-hydroxyphenyl-2H-benzotriazole type. Examples of light stabilizers of the 2-(2-hydroxyphenyl)-1,3,5-triazine type are known from the patent literature, e.g. U.S. Pat. No. 4,619,956, EP-A-434 608, U.S. Pat. No. 5,198,498, U.S. Pat. No. 5,322,868, U.S. Pat. No. 5,369,140, U.S. Pat. No. 5,298,067, WO-94/18278, EP-A-704 437, GB-A-2,297,091 or WO-96/28431. 3,3,5,5 polysubstituted morpholin-2-one derivatives as described in U.S. Pat. No. 6,140,326 are well established light stabilizers for coatings.

The compositions may further comprise other customary additives such as leveling agents, rheology-influencing agents, such as fine-particle silicic acid, layer silicates, urea compounds; thickeners, e.g. based on partially cross-linked carboxy-functional polymers or polyurethanes; defoamers, wetting agents, anti-crater agents, degassing agents, e.g., benzoin, antioxidants.

The compounds may further comprise additives to improve the storage stability such as nitroxyl-based polymerization inhibitors, e.g. Irgastab UV10 and 2,2,6,6-tetramethyl-4-hydroxy-piperidin-1-oxyl (4-hydroxy-TEMPO).

Any thermal initiator known in the art may be used. For example the thermal initiators are peroxides such as dialkyl peroxides, dicumyl peroxide, peroxocarboxylic acids and so on and azo initiators as disclosed in U.S. Pat. No. 5,922,473.

The coating agents may be unpigmented coating agents, e.g. transparent clearcoats or pigmented coating agents.

The coating agents may contain fillers and/or transparent, color- and/or special effect-imparting pigments and/or soluble dyes. Examples of inorganic or organic color-imparting pigments include titanium dioxide, micronized titanium dioxides iron oxide pigments, carbon black, azo pigments, phthalocyanine pigments, quinacridone or pyrrolopyrrole pigments. Examples of special effect-imparting pigments include metallic pigments, e.g., of aluminum, copper or other metals; interference pigments, such as metal oxide-coated metallic pigments, e.g. titanium dioxide-coated or mixed oxide-coated aluminum, coated mica, such as titanium dioxide-coated mica and graphite special-effect pigments. Examples of suitable fillers include silica, aluminum silicate, barium sulfate, calcium carbonate and talc.

Suitable photoinitiators which may be used in addition to the photoinitiators of the formula I to VI are known to those skilled in the art. For example, α-hydroxyketones and α-aminoketones, phenylglyoxalates or phosphine oxides are photoinitiators commonly used in graphic arts applications.

Especially preferred are, for example, the following commercially available photoinitiators:

Darocur 1173: 2-hydroxy-2-methyl-1-phenyl-1-propanone (HMPP) and Oligomeric HMPP, Irgacure 184: 1-hydroxy-cyclohexyl-phenyl ketone, Irgacure 2959: 2-hydroxy-1-[4-(2-hydroxyethoxy)phenyl]-2-methyl-1-propanone, Irgacure 369: 2-benzyl-2-(dimethylamino)-1-[4-(4-morpholinyl)phenyl]-1-butanone, Irgacure 1300: Irgacure 369+Irgacure 651 (benzyldimethylketal), Irgacure 379: 2-(4-methylbenzyl)-2-(dimethylamino)-1-[4-(4-morpholinyl)phenyl]-1-butanone, Irgacure 127: 2-hydroxy-1-{4-[4-(2-hydroxy-2-methyl-propionyl)-benzyl]-phenyl}-2-methyl-propan-1-one, Irgacure 754: oxo-phenyl-acetic acid 1-methyl-2-[2-(2-oxo-2-phenyl-acetoxy)-propoxy]-ethyl ester, Irgacure 819: bis(2,4,6-trimethylbenzoyl)-phenylphosphine oxide, Irgacur 250: 4-isobutylphenyl-4'-methylphenyliodonium hexafluorophosphate, Darocur ITX: 2-isopropylthioxanthone and 4-isopropylthioxanthone, Darocur EDB: ethyl-4-dimethylamino benzoate, Darocur EHA: 2-ethylhexyl-4-dimethylamino benzoate; or mixtures of the above photoinitiators.

The photopolymerisable compositions comprise the photoinitiator advantageously in an amount from 0.05 to 15% by weight, preferably from 0.1 to 8% by weight, based on the composition.

The resulting coating materials of the invention may be conventional coating materials, containing organic solvents, aqueous coating materials, substantially or fully solvent-free and water-free liquid coating materials (100% systems), substantially or fully solvent-free and water-free solid coating materials (powder coating materials), or substantially or fully solvent-free powder coating suspensions (powder slurries).

Non-limiting examples of suitable substrates are, for example, wood, textiles, paper, ceramics, glass, glass fibres, plastics such as polyester, polyethylene terephthalate, polyolefins or cellulose acetate, especially in the form of films, and also metals such as Al, Cu, Ni, Fe, Zn, Mg or Co and GaAs, Si or $SiO_2$.

The coating composition may also be an ink composition. Thus, the substrate is printed with an ink composition to form an ink film on the substrate.

The inventive compositions can be used for various purposes, for example as printing inks, such as screen printing inks, flexographic printing inks or offset printing inks, as clearcoats, as gelcoats, as colour coats, as white coats, e.g. for wood or metal, as powder coatings, as paints, inter alia for paper, water, metal or plastic, as daylight-curable coatings for marking buildings and roads, for photographic reproduction processes, for holographic recording materials, for image recording processes or for the production of printing plates which can be developed using, for example, organic solvents or aqueous-alkaline media, for the production of masks for screen printing, as dental filling materials, as adhesives, as pressure-sensitive adhesives, as laminating resins, as photoresists, e.g. galvanoresists, etch or permanent resists, both liquid and dry films, as photostructurable dielectrics, and as solder stopping masks for electronic circuits, as resists for the preparation of colour filters for any type of screen or for producing structures in the production process of plasma displays and electroluminescence displays, for the production of optical switches, optical gratings (interference gratings), for the preparation of three-dimensional objects by mass curing (UV curing in transparent moulds) or by the stereolithography process, as is described, for example, in U.S. Pat. No. 4,575,330, for the preparation of composite materials (e.g. styrenic polyesters which may contain glass fibres and/or other fibres and other auxiliaries) and other thick-layer materials, for the preparation of gel coats, for the coating or sealing of electronic components or as coatings for optical fibres. The compositions are also suitable for the preparation of optical lenses, e.g. contact lenses and Fresnel lenses, and for the preparation of medical instruments, auxiliaries or implants.

The compositions are also suitable for the preparation of gels having thermotropic properties. Such gels are described, for example, in DE 19700064 and EP 678534.

Furthermore, the compositions can be used in dry-film paints, as are described, for example, in Paint & Coatings Industry, April 1997, 72 or Plastics World, Volume 54, No. T, page 48(5).

Preparation of the Coating

The components of the formulation and optionally further additives are applied uniformly to a substrate by means of known coating techniques, for example by spin-coating, immersion, knife coating, curtain pouring, brush application or spraying, especially by electrostatic spraying and reverse-roll coating, and also by electrophoretic deposition. The quantity applied (coat thickness) and the nature of the substrate (layer support) are dependent on the desired field of application. The range of coat thicknesses generally comprises values from 0.1 μm to 1 mm for gel coats and more than 1 mm for composites.

A preferred field of use comprises overprint varnishes and also pigmented thin coatings (layer thickness<20 μm), for example printing inks that are used in printing methods such as, for example, flexographic printing, offset printing, screen printing, intaglio printing, letterpress printing, tampon printing and inkjet printing.

Overprint varnishes typically comprise ethylenically unsaturated compounds such as oligomeric and/or monomeric acrylates. Amine acrylates may also be included.

As mentioned hereinbefore, the overprint varnishes and printing inks may also comprise further photoinitiators and coinitiators.

The invention relates also to the use of the above-described composition and to a process for the production of pigmented and non-pigmented surface coatings, overprint varnishes, powder coatings, printing inks, inkjet inks, gel coats, composite materials or glass fibre coatings.

The invention relates also to a coated substrate which has been coated on at least one surface with a composition as described above.

The following Examples further illustrate the invention:

EXAMPLES 1) 2-Methyl-1-p-tolyl-propane-1-one, Friedel-Crafts Reaction, AlCl₃ Added in Solid Form

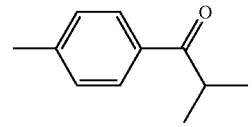

53.3 g (0.50 mol) of isobutyryl chloride and 100 g of toluene are introduced into a 350 ml reaction flask. The solution is cooled to 5-0° C. Then, over about three hours, 73.3 g (0.55 mol) of aluminium chloride are added in small portions at 0-5° C. After the evolution of HCl gas has ceased, the reaction is checked using GC. The reddish reaction solution is then poured into ice and water and stirred to complete the reaction. The two phases are separated in a separating funnel. The organic phase is washed with water and then concentrated using a vacuum rotary evaporator, resulting in 78.5 g of a slightly yellowish liquid, which is checked using GC, TLC and a ¹H NMR spectrum. The product, 2-methyl-1-p-tolyl-propan-1-one, is used directly in the next reaction.

2) 2-Bromo-1-(4-bromomethyl-phenyl)-2-methyl-propane-1-one, Bromination

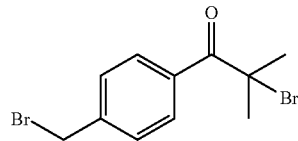

78.5 g (0.484 mol) of 2-methyl-1-p-tolyl-propan-1-one and 200 g of carbon tetrachloride are introduced into a 750 ml reaction flask. Then, over about two hours, 77 g of bromine are added dropwise at about 25° C. The reaction is checked using a ¹H NMR spectrum. The resulting product, 2-bromo-2-methyl-1-p-tolyl-propan-1-one, is further brominated using 77.7 g of bromine in carbon tetrachloride at 50-60° C. over about three hours with the aid of a 150 Watt daylight lamp. The reaction is checked using a ¹H NMR spectrum. The resulting product, 2-bromo-1-(4-bromomethyl-phenyl)-2-methyl-propan-1-one, still contains starting compound, 2-bromo-2-methyl-1-p-tolyl-propan-1-one, and the tribromine compound, 2-bromo-1-(4-dibromomethyl-phenyl)-2-methyl-propan-1-one. The solution is concentrated, diluted with toluene and concentrated again, resulting in 173.5 g of oil which still contains a small amount of toluene. The crude product, 2-bromo-1-(4-bromomethyl-phenyl)-2-methyl-propan-1-one, is used in the next reaction step without further purification.

3) 2-Hydroxy-1-(4-hydroxymethyl-phenyl)-2-methyl-propane-1-one and the dimer 2-hydroxy-1-{4-[4-(2-hydroxy-2-methyl-propionyl)-benzyloxymethyl]-phenyl}-2-methyl-propane-1-one, Hydrolysis Example 3a

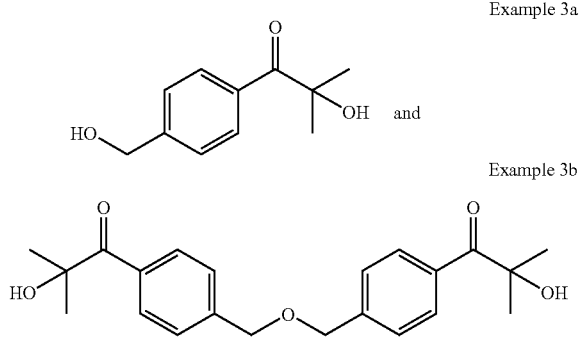

Example 3b

In a nitrogen atmosphere, 30.1 g (84 mmol t.q.) of 2-bromo-1-(4-bromomethyl-phenyl)-2-methyl-propan-1-one, 150 g of dioxane and 0.5 g of tetrabutylammonium bromide, dissolved in 15 g of water, are introduced into a 500 ml reaction flask. Then, at about 80° C., an initial amount of 34.7 g of 15% sodium hydroxide solution is added dropwise over about two hours. The reaction solution is alkaline, about pH 9-10. The reaction is checked using a $^1$H NMR spectrum. The intermediate formed in part, 1-(4-bromomethyl-phenyl)-2-hydroxy-2-methyl-propan-1-one, accumulates and, despite the addition of sodium hydroxide solution, the reaction stops before completion. The addition of sodium hydroxide solution is then interrupted and the salt-containing aqueous phase is separated off. Further 15% sodium hydroxide solution is slowly added dropwise at about 80° C. to the organic phase, totalling 44.8 g (0.164 mol) of 15% sodium hydroxide solution. The bromide, 1-(4-bromomethyl-phenyl)-2-hydroxy-2-methyl-propan-1-one, slowly disappears and the pH of the reaction solution remains at about 10. The salt-containing aqueous phase is again separated off and the organic phase is concentrated, resulting in 13.4 g of yellow oil which, in the $^1$H NMR spectrum, is a product mixture. The oil is separated on a silica gel column. A mixture of ethyl acetate: mixed hexanes 1:1 is used as eluant. Three liquid products are obtained and confirmed using a $^1$H NMR spectrum: 2-hydroxy-1-(4-hydroxymethyl-phenyl)-2-methyl-propan-1-one (Example 3a) as main product, the dimer 2-hydroxy-1-{4-[4-(2-hydroxy-2-methyl-propionyl)-benzyloxymethyl]-phenyl}-2-methyl-propan-1-one (Example 3b) as subsidiary product and, as components of a further small fraction which is separated by HPLC, 2-hydroxy-2-methyl-1-p-tolyl-propan-1-one and 1-(4-dibromomethyl-phenyl)-2-hydroxy-2-methyl-propan-1-one.

Example 3a (2-Hydroxy-1-(4-hydroxymethyl-phenyl)-2-methyl-propane-1-one) is a crystalline compound, melting point 45-48° C.

Elemental analysis for 2-hydroxy-1-(4-hydroxymethyl-phenyl)-2-methyl-propan-1-one: Example 3a

|  | % C |  | % H |
|---|---|---|---|
| calculated: | 68.02 | calculated: | 7.27 |
| found: | 68.02 | found: | 7.23 |

Elemental analysis for 2-hydroxy-1-{4-[4-(2-hydroxy-2-methyl-propionyl)-benzloxymethyl]-phenyl}-2-methyl-propan-1-one: Example 3b

|  | % C |  | % H |
|---|---|---|---|
| calculated: | 71.33 | calculated: | 7.07 |
| found: | 71.26 | found: | 7.05 |

4) 2-Hydroxy-1-(4-methoxymethyl-phenyl)-2-methyl-propan-1-one, Methanolysis

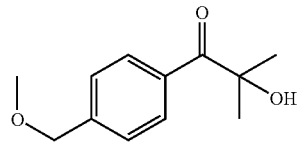

In a nitrogen atmosphere, 15.0 g (0.1125 mol) of 30% conc. sodium hydroxide solution and 15 ml of deionised water and 15 g of methanol are introduced into a 200 ml reaction flask and heated to 55° C. A solution of 14.3 g (40 mmol t.q.) of 2-bromo-1-(4-bromomethyl-phenyl)-2-methyl-propan-1-one, 15 g of toluene and 15 g of methanol is then added dropwise over about 15 minutes and subsequently stirred at 55-60° C. The reaction is checked using a $^1$H NMR spectrum. The emulsion is then cooled and adjusted to pH 1-2 using 16% hydrochloric acid dropwise and is subsequently stirred for about 30 minutes. The reaction is checked using a $^1$H NMR spectrum. The aqueous phase is separated off in a separating funnel and is extracted twice with 40 g of toluene. The organic phase is washed with a small amount of water, combined with the organic phases and then concentrated in vacuo, resulting in 8.3 g of thin, yellowish oil, which is checked using TLC and a $^1$H NMR spectrum. The crude product is separated on a silica gel column. A mixture of ethyl acetate: mixed hexanes 1:3 is used as eluant. Four liquid products are obtained and confirmed using a $^1$H NMR spectrum: 2-hydroxy-1-(4-methoxymethyl-phenyl)-2-methyl-propan-1-one as main product and small amounts of 2-hydroxy-2-methyl-1-p-tolyl-propan-1-ne, 1-(4-dibromomethyl-phenyl)-2-hydroxy-2-methyl-propan-1-one and 4-(2-hydroxy-2-methyl-propionyl)-benzaldehyde as subsidiary products.

Elemental analysis for 2-hydroxy-1-(4-methoxymethyl-phenyl)-2-methyl-propan-1-one:

|  | % C |  | % H |
|---|---|---|---|
| calculated: | 69.21 | calculated: | 7.74 |
| found: | 68.70 | found: | 7.48 |

5) 2-Methoxy-2-(4-methoxymethyl-phenyl)-3,3-dimethyl-oxirane, Epoxy Ether Formation

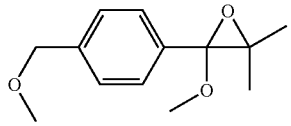

In a nitrogen atmosphere, 37.8 g (210 mmol) of 30% sodium methanolate solution in methanol are introduced into a 200 ml reaction flask. 30.1 g (84 mmol t.q.) of 2-bromo-1-(4-bromomethyl-phenyl)-2-methyl-propan-1-one, diluted with 25 g of toluene, are then added dropwise at 25-30° C. The suspension is then stirred and the reaction is checked using a $^1$H NMR spectrum. Starting compound is no longer present. The suspension is filtered, the NaBr is washed with toluene, and the filtrate is concentrated and dried in vacuo. 19.6 g of yellowish oil are obtained, which in the $^1$H NMR spectrum is identified as 2-methoxy-2-(4-methoxymethyl-phenyl)-3,3-dimethyl-oxirane. The crude product, 2-methoxy-2-(4-methoxy-methyl-phenyl)-3,3-dimethyl-oxirane, is used in the next reaction step without further purification.

6) 1-(4-Methoxymethyl-phenyl)-2-methyl-2-morpholin-4-yl-propan-1-one, Aminolysis of the Epoxy Ether

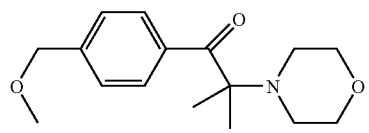

In a nitrogen atmosphere, 9.7 g (42 mmol t.q.) of 2-methoxy-2-(4-methoxymethyl-phenyl)-3,3-dimethyl-oxirane and 36.6 g of (420 mmol) of morpholine are introduced into a 100 ml reaction flask. The mixture is then heated and maintained at reflux (130° C.) for 16 hours. The methanol that forms is removed at about 130° C. in a gentle current of nitrogen. The solution is then concentrated using a vacuum rotary evaporator. 8.9 g of dark-yellow oil are obtained. Dissolution in toluene and extraction with dilute hydrochloric acid solution are carried out. Toluene is added to the aqueous phase, and the pH is adjusted to 10 with 15% sodium hydroxide solution. The phases are separated and the aqueous phase is extracted again with toluene. The toluene phases are combined and washed with water, concentrated using a vacuum rotary evaporator and dried in vacuo. 2.0 g of yellow oil are obtained, which, according to the $^1$H NMR spectrum, is 1-(4-methoxymethyl-phenyl)-2-methyl-2-morpholin-4-yl-propan-1-one.

7) 2-Methyl-2-morpholin-4-yl-1-(4-morpholin-4-ylmethyl-phenyl)-propan-1-one, Aminolysis of the Bromine Derivative

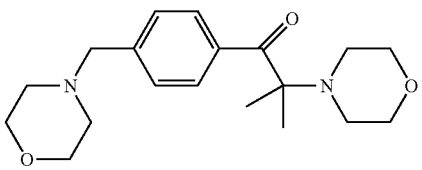

In a nitrogen atmosphere, 6.5 g (20 mmol t.q.) of 2-bromo-1-(4-bromomethyl-phenyl)-2-methyl-propan-1-one, 5.0 g (57 mmol) of morpholine and 5 g of dioxane are heated in a 50 ml round-bottom flask at about 85° C. for 12 hours. The mixture is then concentrated in vacuo and subsequently diluted with 30 ml of toluene.

In a nitrogen atmosphere, 18.0 g (0.1 mol) of 30% sodium methanolate solution in methanol are introduced into a 100 ml reaction flask. The toluene solution is added dropwise over 15 minutes, with cooling (0-15° C.), and stirring is subsequently carried out for several hours. The white suspension is concentrated to one third in vacuo and filtered. 18.0 g (0.2 mol) of morpholine are added to the filtrate; the mixture is heated and maintained at reflux (130° C.) for 16 hours. The methanol that forms is removed at about 130° C. in a gentle current of nitrogen. The solution is then concentrated using a vacuum rotary evaporator, diluted with toluene and extracted with dilute hydrochloric acid solution. Ethyl acetate is added to the aqueous phase, which is then rendered basic using 15% sodium hydroxide solution. The organic phase is separated off and the aqueous phase is again extracted with ethyl acetate. The organic phases are combined and washed with a small amount of water, concentrated using a vacuum rotary evaporator and dried in vacuo. 2.4 g of yellowish oil are obtained, which, according to the $^1$H NMR spectrum, is 2-methyl-2-morpholin-4-yl-1-(4-morpholin-4-ylmethyl-phenyl)-propan-1-one.

8) 2-Hydroxy-1-{4-[2-(2-hydroxy-ethoxy)-ethoxymethyl]-phenyl}-2-methyl-propan-1-one, Alcoholysis of the Bromine Derivative

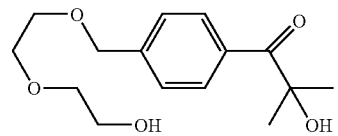

6.5 g (20 mmol t.q.) of 2-bromo-1-(4-bromomethyl-phenyl)-2-methyl-propan-1-one and 8.5 g (80 mmol) of diethylene glycol in 15 g of dioxane are introduced into a 50 ml reaction vessel. A small spatula tip of p-toluenesulfonic acid is then added. The solution is processed, in portions, in the "Emry Optimizer" microwave reactor (from Personal Chemistry, Uppsala, Sweden) for two hours at 140° C. The reaction is checked using a $^1$H NMR sample. Dilution with toluene and water is then carried out. The toluene phase is separated off and concentrated. 6.5 g of crude product are obtained and checked using a $^1$H NMR sample. The aqueous phase is extracted with ethyl acetate. The ethyl acetate solution is dried in vacuo and checked using a ¹H NMR sample. 2.0 g of yellowish oil are obtained, which, according to the ¹H NMR spectrum, is 2-hydroxy-1-{4-[2-(2-hydroxy-ethoxy)-ethoxymethyl]-phenyl}-2-methyl-propan-1-one.

9) 1-(4-Bromomethyl-phenyl)-2-hydroxy-2-methyl-propan-1-one, Selective Hydrolysis of the Bromine Derivative

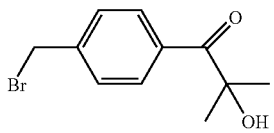

In a nitrogen atmosphere, 30.1 g (84 mmol t.q.) of 2-bromo-1-(4-bromomethyl-phenyl)-2-methyl-propan-1-one and 30 g of dioxane are introduced into a 100 ml reaction flask. 10.5 g (79 mmol) of 30% sodium hydroxide solution are added dropwise thereto at room temperature over about 20 minutes. After subsequently stirring for 30 minutes, the reaction is checked using a ¹H NMR spectrum. The reaction mixture is concentrated using a vacuum rotary evaporator, diluted with a small amount of water and then extracted three times using 50 ml of toluene each time. The toluene solution is concentrated using a vacuum rotary evaporator. 20.6 g of a yellowish oil are obtained and checked using a ¹H NMR spectrum. For purification and characterisation, 2.0 g of that oil are separated on a preparative HPLC column containing LiChrospher Si 60 (12 μm) silica gel from Merck. A mixture of 70% n-heptane and 30% ethyl acetate is used as eluant. 1.1 g of white crystals are isolated in the main fraction, which melt at 56-58° C. and, according to the ¹H NMR spectrum, are 1-(4-bromomethyl-phenyl)-2-hydroxy-2-methyl-propan-1-one. The crude product itself is further reacted without further purification.

10) 2-Hydroxy-2-methyl-1-(4-morpholin-4-ylmethyl-phenyl)-propan-1-one, Aminolysis of the Monobromine Derivative

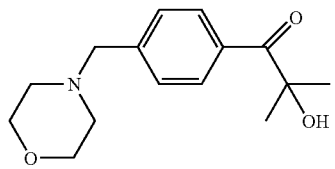

In a nitrogen atmosphere, 5.1 g (20 mmol t.q.) of crude 1-(4-bromomethyl-phenyl)-2-hydroxy-2-methyl-propan-1-one and 20 g of dioxane are introduced into a 100 ml reaction flask. 1.7 g (20 mmol) of morpholine are added dropwise thereto at room temperature, whilst cooling slightly. White crystals precipitate out. Subsequent stirring for two hours at room temperature is carried out. The reaction is checked using a ¹H NMR spectrum. A further 0.9 g (10 mmol) of morpholine is then added dropwise and again subsequently stirred. The reaction is again checked using a ¹H NMR spectrum. The reaction mixture is concentrated using a vacuum rotary evaporator and diluted with 20 g of water and 30 g of ethyl acetate. The phases are separated. The aqueous phase is extracted twice using 10 g of ethyl acetate each time. The organic phases are combined and concentrated using a vacuum rotary evaporator. 5.1 g of a dark-yellow oil are obtained, which is purified on a silica gel column. A mixture of ethyl acetate: mixed hexanes 1:1, rendered basic with a few drops of triethylamine, is used as eluant. In the main fraction, 3.4 g of yellowish oil are isolated, which, according to the ¹H NMR spectrum, is confirmed as 2-hydroxy-2-methyl-1-(4-morpholin-4-ylmethyl-phenyl)-propan-1-one.

11) Carbonic acid 4-(2-hydroxy-2-methyl-propionyl)-benzyl ester methyl ester, Carbonate Formation from Hydroxy Ketone

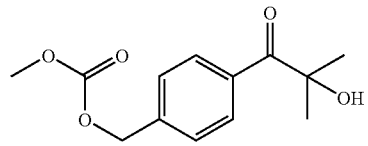

Under argon gas, 3.0 g (15.5 mmol) of 2-hydroxy-1-(4-hydroxymethyl-phenyl)-2-methyl-propan-1-one and 1.5 g (19 mmol) of pyridine in 50 ml of tetrahydrofuran are introduced into a 100 ml reaction flask. The pale-yellow solution is cooled to 0° C., and 1.6 g (17 mmol) of methyl chloroformate diluted with 5 ml of tetrahydrofuran are added dropwise between 0 and 2° C. over 45 minutes. A whitish-yellow suspension is formed, which is further stirred overnight in an ice bath. After warming up to room temperature, the reaction mixture is poured into 50 ml of water and extracted with ethyl acetate. The organic phase is dried over sodium sulfate and concentrated. The crude product is purified by means of flash chromatography on silica gel (eluant: mixed hexanes:ethyl acetate 2:1). 2.3 g of carbonic acid 4-(2-hydroxy-2-methyl-propionyl)-benzyl ester methyl ester are obtained as a pale-yellow liquid. The structure is confirmed using a ¹H NMR spectrum.

12) {6-[4-(2-Hydroxy-2-methyl-propionyl)-benzyloxycarbonylamino]-hexyl}carbamic acid 4-(2-hydroxy-2-methyl-propionyl)-benzyl ester, Preparation of an Urethane Starting from Hydroxyketone

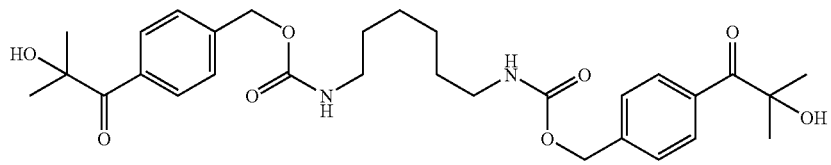

In an argon atmosphere, 4.3 g (22 mMol) of 2-hydroxy-1-(4-hydroxymethyl-phenyl)-2-methyl-propan-1-one and 0.5 g (4.5 mMol) of 1,4-dizabicyclo[2.2.2]octane and 50 ml of dioxane are introduced into a 200 ml reaction flask. The solution is heated to 100° C. A solution of 1.7 g (10 mMol) of hexamethylendiisocyanate in 25 ml dioxane is added slowly. The reaction mixture is maintained and stirred at reflux for 20 h. The reaction is checked using IR-spectrometry. No free isocyanate is present in the reaction mixture. The reaction mixture is cooled and concentrated using a vacuum rotary. 7.2 g of an oil are obtained. The oil starts to crystallize after a time. The structure of the compound is analyzed using $^1$H-NMR. For purification the crude product ({6-[4-(2-Hydroxy-2-methyl-propionyl)-benzyloxycarbonyl-amino]-hexyl}-carbamic acid 4-(2-hydroxy-2-methyl-propionyl)-benzyl ester) is separated on a silica gel column. A mixture of ethyl acetate/hexane 2:1 is used as eluent. 4.3 g of white crystals are obtained. According to $^1$H-NMR-Spektra I{6-[4-(2-Hydroxy-2-methyl-propionyl)-benzyloxycarbony-lamino]-hexyl}-carbamic acid 4-(2-hydroxy-2-methyl-propionyl)-benzyl ester is obtained.

13. 1-(3,4-Dimethyl-phenyl)-2-methyl-propan-1-one, Friedel-Crafts Reaction

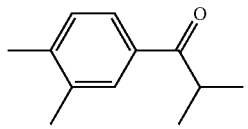

In a nitrogen atmosphere, 213.1 g (2.0 mol) of isobutyryl chloride and 400 g of o-xylene are introduced into a 1.5 litre reaction flask. The solution is cooled to 5-0° C. Then, over about three hours, 293.3 g (2.2 mol) of aluminium chloride are added in small portions at 0-5° C. After the evolution of HCl gas has ceased, the reaction is checked using GC. The dark-red reaction solution is then poured into ice and water and stirred to complete the reaction. The two phases are separated in a separating funnel. The organic phase is washed with water and is then concentrated using a vacuum rotary evaporator. The last remnants of solvent are removed under a high vacuum. 329.1 g of faintly yellowish oil remain behind. The product is checked using GC and a $^1$H NMR spectrum. The product, 1-(3,4-dimethyl-phenyl)-2-methyl-propan-1-one, is used directly in the next reaction.

14) 1-(3,4-Bisbromomethyl-phenyl)-2-bromo-2-methyl-propan-1-one, Bromination

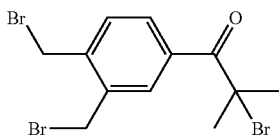

In a nitrogen atmosphere, 176.3 g (1.0 mol t.q.) of 1-(3,4-dimethyl-phenyl)-2-methyl-propan-1-one and 200 g of carbon tetrachloride are introduced into a 750 ml reaction flask. The solution is heated to about 50° C. and brominated at 50-60° C. with the aid of a 150 Watt daylight lamp using 479.5 g (3.0 mol) of bromine in portions over about 20 hours. The reaction is checked using a $^1$H NMR spectrum. The mixture formed comprises the desired tribromine compound, 1-(3,4-bisbromomethyl-phenyl)-2-bromo-2-methyl-propan-1-one, and still comprises a small amount of the intermediates, 2-bromo-1-(4-bromomethyl-3-methyl-phenyl)-2-methyl-propan-1-one, 2-bromo-1-(3-bromomethyl-4-methyl-phenyl)-2-methyl-propan-1-one, 2-bromo-1-(4-dibromomethyl-3-methyl-phenyl)-2-methyl-propan-1-one and 2-bromo-1-(3-bromomethyl-4-dibromomethyl-phenyl)-2-methyl-propan-1-one. The solution is concentrated using a vacuum rotary evaporator, diluted with toluene and concentrated again, resulting in 402 g of a reddish-brown oil. Addition of mixed hexanes and crystallisation are carried out. The crystals are filtered off, washed with mixed hexanes and dried in vacuo. 123.3 g of crystals are obtained and checked using a $^1$H NMR spectrum. For purification, they are re-crystallised again using 185 g of mixed hexanes, resulting in 83.2 g of white crystals, which melt at 91.0-91.7° C. and which, according to the $^1$H NMR spectrum, are 1-(3,4-bisbromomethyl-phenyl)-2-bromo-2-methyl-propan-1-one. A further 119.4 g of crystals of lower purity are isolated from the mother liquors.

15) 2-(3,4-Bismethoxymethyl-phenyl)-2-methoxy-3,3-dimethyl-oxirane, Epoxy Ether Formation

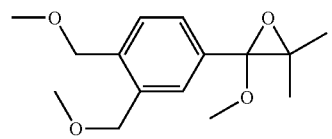

In a nitrogen atmosphere, 37.8 g (210 mmol) of 30% sodium methanolate solution in methanol are introduced into a 350 ml reaction flask. Then, over about an hour, 24.8 g (60 mmol) of crystalline 1-(3,4-bisbromomethyl-phenyl)-2-bromo-2-methyl-propan-1-one, dissolved in 100 g of toluene, are added dropwise whilst cooling slightly at 10-20° C. The suspension is subsequently stirred and the reaction is checked using a $^1$H NMR spectrum. The reaction mixture is heated to about 35° C. and subsequently stirred overnight. The pH remains basic. According to the $^1$H NMR spectrum, all the starting compound has now reacted. The suspension is filtered, the filtrate is concentrated to half using a vacuum rotary evaporator and the remaining salt in the solution is again filtered off. The filtrate is concentrated in a vacuum rotary evaporator. 14.4 g of yellowish oil are obtained, which is identified in the $^1$H NMR spectrum as 2-(3,4-bismethoxymethyl-phenyl)-2-methoxy-3,3-dimethyl-oxirane. The crude product, 2-(3,4-bismethoxymethyl-phenyl)-2-methoxy-3,3-dimethyl-oxirane, is used in the next reaction step without further purification.

16) 1-(3,4-Bismethoxymethyl-phenyl)-2-methyl-2-morpholin-4-yl-propan-1-one and 1-(3,4-bismethoxymethyl-phenyl)-2-hydroxy-2-methyl-propan-1-one, Aminolysis

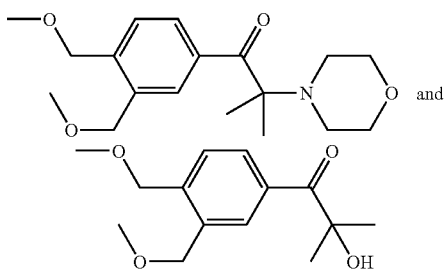

In an argon atmosphere, 14.4 g (54 mmol) of 2-(3,4-bismethoxymethyl-phenyl)-2-methoxy-3,3-dimethyl-oxirane and 47.0 g (540 mmol) of morpholine are introduced into a 100 ml round-bottom flask. The solution is heated at reflux (130° C.) and the methanol that forms is removed in a gentle current of argon. After four hours, a further 17 g of morpholine are added. After 19 hours, the reaction is checked using GC and a $^1$H NMR spectrum. In addition to the desired product, the hydroxy ketone has also been formed. The reaction mixture is concentrated using a vacuum rotary evaporator, resulting in 13.0 g of crude product. Half of the mixture is purified on a silica gel column. A mixture of ethyl acetate: mixed hexanes 1:1 is used as eluant. Two products are separated and isolated, which are identified in the $^1$H NMR spectrum as 1-(3,4-bismethoxymethyl-phenyl)-2-methyl-2-morpholin-4-yl-propan-1-one and as 1-(3,4-bismethoxymethyl-phenyl)-2-hydroxy-2-methyl-propan-1-one. The other half of the mixture is dissolved in toluene and extracted with dilute hydrochloric acid solution. According to the $^1$H NMR spectrum, 1-(3,4-bismethoxymethyl-phenyl)-2-hydroxy-2-methyl-propan-1-one remains in the toluene. The toluene solution is concentrated using a vacuum rotary evaporator. The hydrochloric acid solution is made basic and extracted with ethyl acetate. The ethyl acetate solution is concentrated using a vacuum rotary evaporator. According to the $^1$H NMR spectrum, 1-(3,4-bismethoxymethyl-phenyl)-2-methyl-2-morpholin-4-yl-propan-1-one remains as residue. The products that belong together are combined.

17) 1-(1,3-Dihydro-isobenzofuran-5-yl)-2-hydroxy-2-methyl-propan-1-one, Hydrolysis with Water

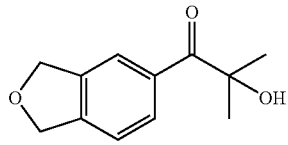

In a nitrogen atmosphere, 12.4 g (30 mmol) of crystallised 1-(3,4-bisbromomethyl-phenyl)-2-bromo-2-methyl-propan-1-one and 30 g of dioxane are introduced into a 100 ml reaction flask and heated. At 40° C., dissolution is complete 6 g of water are added, and heating to 85° C. is carried out. The pH becomes highly acid. The reaction mixture is processed in portions in the "Emry Optimizer" microwave reactor (from Personal Chemistry, Uppsala, Sweden) for two hours at 140° C. The reaction is checked using a $^1$H NMR spectrum. The reaction mixture now comprises about 63% in the form of the furan derivative. 13.3 g (0.1 mol) of 30% sodium hydroxide solution and 7 g of water are then added to the reaction mixture and heating overnight at reflux (85° C.) is carried out. According to the $^1$H NMR spectrum, all starting material has now been reacted. The reaction mixture is concentrated using a vacuum rotary evaporator, diluted with water and extracted twice with 50 ml of toluene and twice with 50 ml of ethyl acetate. The organic phases are combined and concentrated in vacuo. 4.4 g of a yellow oil are obtained. Purification on a silica gel column is carried out. A mixture of ethyl acetate: mixed hexanes 1:3 is used as eluant. In the main fraction there are obtained 2.3 g of a yellowish oil, which, according to the $^1$H NMR spectrum, is 1-(1,3-dihydro-isobenzofuran-5-yl)-2-hydroxy-2-methyl-propan-1-one

18) Cyclohexyl-(3,4-dimethyl-phenyl)-methanone, Friedel-Crafts Reaction

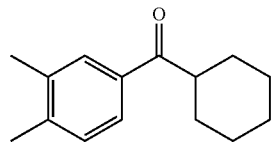

In a nitrogen atmosphere, 146.7 g (1.1 mol) of aluminium chloride and 300 g (2.8 mol) of o-xylene are introduced into a 750 ml reaction flask. The suspension is cooled to 5-0° C. Then, over about four hours, 146.6 g (1.0 mol) of cyclohexanecarboxylic acid chloride are added dropwise at 0-5° C. The reddish-yellow solution is then stirred overnight at room temperature to complete the reaction. The reaction is checked using GC and the $^1$H NMR spectrum. The reaction solution is then poured into ice and water and stirred to complete the reaction. The two phases are separated in a separating funnel. The organic phase is washed with water and with dilute sodium hydroxide solution and is then concentrated using a vacuum rotary evaporator, resulting in 217.2 g of yellowish oil, which is checked using GC and the $^1$H NMR spectrum. The product, cyclohexyl-(3,4-dimethyl-phenyl)-methanone, is used directly in the next reaction.

19) (1-Bromo-cyclohexyl)-(4-bromomethyl-3-methyl-phenyl)-methanone, Bromination

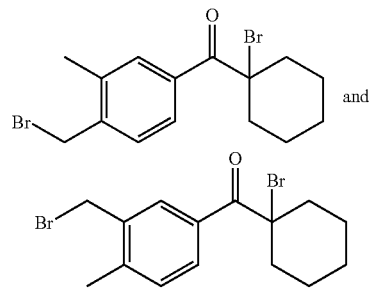

In a nitrogen atmosphere, 54.3 g (0.25 mol t.q.) of cyclohexyl-(3,4-dimethyl-phenyl)-methanone and 250 g of puregrade acetic acid are introduced into a 750 ml reaction flask and heated with the aid of a 150 Watt daylight lamp to 35° C.

79.9 g (0.50 mol) of bromine are slowly added dropwise. The temperature increases to 95-100° C. The reaction is checked using the ¹H NMR spectrum. After an hour 40 g of bromine have been added. HBr gas is evolved. After four hours, all the bromine has been added. The yellow solution is cooled and concentrated using a vacuum rotary evaporator. 101.4 g of dark-yellow oil are obtained. According to the ¹H NMR spectrum, the reaction mixture formed comprises, as main product, the desired dibromine compound, (1-bromo-cyclohexyl)-(4-bromomethyl-3-methyl-phenyl)-methanone, and, as isomer, (1-bromo-cyclohexyl)-(3-bromomethyl-4-methyl-phenyl)-methanone, in a ratio of about 2:1 and still comprises a small amount of the monobromine compound, (1-bromo-cyclohexyl)-(3,4-dimethyl-phenyl)-methanone, and of the tribromine compound, (3,4-bisbromomethyl-phenyl)-(1-bromo-cyclohexyl)-methanone. The crude product is used in the next reaction without further purification.

20) (1-Hydroxy-cyclohexyl)-(4-hydroxymethyl-3-methyl-phenyl)-methanone and (1-hydroxy-cyclohexyl)-(3-hydroxymethyl-4-methyl-phenyl)-methanone, Hydrolysis

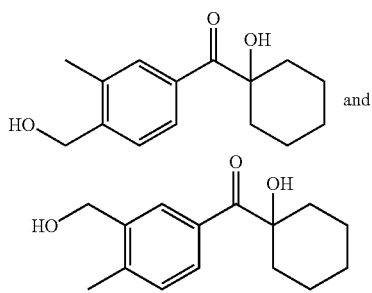

and

In an argon atmosphere, 73.0 g (0.18 mol t.q.) of the reaction mixture comprising the dibromine compound, (1-bromo-cyclohexyl)-(4-bromomethyl-3-methyl-phenyl)-methanone, and 100 g of dioxane are introduced into a 350 ml reaction flask. Then, over about two hours, 96 g of 15% sodium hydroxide solution are added dropwise at about 80° C. The reaction solution is alkaline and is stirred at about 80° C. for 20 hours. The reaction is checked using a ¹H NMR spectrum. It is not complete. The reaction mixture is cooled and the aqueous phase is separated off. 19.2 g of 15% sodium hydroxide solution are again added to the organic phase and further stirring is carried out at about 80° C. under an argon atmosphere. After about 20 hours, according to a ¹H NMR spectrum, hydrolysis is complete. The reaction mixture is cooled and the aqueous phase is separated off again. The aqueous phase is extracted three times with ethyl acetate. The organic phases are concentrated using a vacuum rotary evaporator. 40.4 g of a yellowish oil are obtained, which, in the ¹H NMR spectrum, is a product mixture. The oil is separated on a silica gel column. A mixture of ethyl acetate: mixed hexanes 1:5 is used as eluant. Three liquid fractions are separated and confirmed using a ¹H NMR spectrum: 19.0 g, as the main product, of (1-hydroxy-cyclohexyl)-(4-hydroxymethyl-3-methyl-phenyl)-methanone (Example 20a) and its isomer, (1-hydroxy-cyclohexyl)-(3-hydroxymethyl-4-methyl-phenyl)-methanone, in a ratio of 2:1. 8.0 g of (3,4-dimethyl-phenyl)-(1-hydroxy-cyclohexyl)-methanone are also isolated as subsidiary product. Further subsidiary products that are separated are the mixture of dimers having, as main component, {4-[4-(1-hydroxy-cyclohexanecarbonyl)-2-methyl-benzyloxymethyl]-3-methyl-phenyl}(1-hydroxy-cyclohexyl)-methanone and, as subsidiary components, the two isomers, {3-[4-(1-hydroxy-cyclohexanecarbonyl)-2-methyl-benzyloxymethyl]-4-methyl-phenyl}(1-hydroxy-cyclohexyl)-methanone and {3-[5-(1-hydroxy-cyclohexanecarbonyl)-2-methyl-benzyloxymethyl]-4-methyl-phenyl}(1-hydroxy-cyclohexyl)-methanone (Example 20b) together with the furan derivative, (1,3-dihydro-isobenzofuran-5-yl)-(1-hydroxy-cyclohexyl)-methanone. The furan derivative, (1,3-dihydro-isobenzofuran-5-yl)-(1-hydroxy-cyclohexyl)-methanone, is separated from the mixture of dimers (Example 20b) by additional separation on a silica gel column. The furan derivative is crystallised in toluene and melts at 103-104° C.

21) 1-(4-Isobutyl-phenyl)-2-methyl-propan-1-one, Friedel-Crafts Reaction AlCl₃ Added in Solid Form

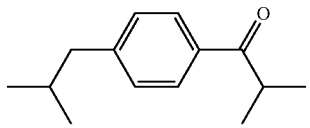

100.7 g (0.75 mol) of isobutylbenzene and 400 ml of chlorobenzene are introduced into a 750 ml reaction flask. 84.2 g (0.79 mol) of isobutyryl chloride are then added and the solution is cooled to 5-0° C. Then, at 0-5° C., over about three hours, 110.0 g (0.82 mol) of aluminium chloride are added in small portions. HCl gas is evolved. Then the mixture is subsequently stirred overnight at an internal temperature of 0-5° C., and the reaction is then checked using GC. The brownish-green reaction solution is then poured into ice and water and stirred to complete the reaction. The two phases are separated in a separating funnel. The organic phase is washed with water and then concentrated using a vacuum rotary evaporator, resulting in 145 g of yellow liquid. The liquid is checked using GC, TLC and a ¹H NMR spectrum and subjected to fractional distillation in vacuo at about 3 mbar and 89° C. The main fraction yields 120.5 g of colourless product, 1-(4-isobutyl-phenyl)-2-methyl-propan-1-one. The product is used directly in the next reaction.

22) 2-Bromo-1-[4-(1-bromo-2-methyl-propyl)-phenyl]-2-methyl-propan-1-one, Bromination

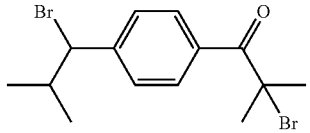

102.2 g (0.50 mol t.q.) of 1-(4-isobutyl-phenyl)-2-methyl-propan-1-one are dissolved in 200 ml of carbon tetrachloride in a 750 ml reaction flask. 80 g of bromine are then dissolved in 50 ml of carbon tetrachloride and, at about 25° C., added dropwise over about two hours. The reaction is checked using TLC and a ¹H NMR spectrum. The product formed, 2-bromo-1-(4-isobutyl-phenyl)-2-methyl-propan-1-one, is further brominated in carbon tetrachloride at 50-60° C. over about five hours using 80 g of bromine dissolved in 50 ml of carbon tetra-chloride, in the course of which three 0.5 g portions of azoisobutyronitrile are added as catalyst. The reaction is checked using a $^1$H NMR spectrum. The solution is concentrated in vacuo, diluted with toluene and concentrated again, resulting in 178.4 g of an orange oil which still contains a small amount of toluene. The crude product, 2-bromo-1-[4-(1-bromo-2-methyl-propyl)-phenyl]-2-methyl-propan-1-one, is used in the next reaction step without further purification.

23) 2-Hydroxy-1-[4-(1-hydroxy-2-methyl-propyl)-phenyl]-2-methyl-propan-1-one, Hydrolysis

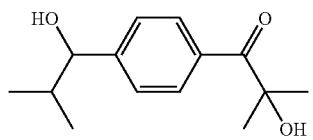

In a nitrogen atmosphere, 178.4 g (0.5 mol t.q.) of 2-bromo-1-[4-(1-bromo-2-methyl-propyl)-phenyl]-2-methyl-propan-1-one, 150 g of toluene and 1.0 g of tetrabutylammonium hydrogen sulfate, dissolved in 20 g of water, are introduced into a 750 ml reaction flask. Then, at about 80° C., 266.7 g (1.0 mol) of 15% sodium hydroxide solution are added dropwise over about two hours. The reaction mixture is stirred overnight at 75-80° C. to complete the reaction. The reaction is checked using a $^1$H NMR spectrum. The reaction mixture is cooled and the aqueous salt phase is separated off. The toluene solution is washed with a small amount of water and concentrated in vacuo. The oil is chromatographed on a silica gel column, using a mixture of ethyl acetate: mixed hexanes 1:1 as eluant and resulting in 101.5 g of yellow oil which, according to the $^1$H NMR spectrum, is 2-hydroxy-1-[4-(1-hydroxy-2-methyl-propyl)-phenyl]-2-methyl-propan-1-one.

Elemental analysis for 2-hydroxy-1-[4-(1-hydroxy-2-methyl-propyl)-phenyl]-2-methyl-propan-1-one.

|  | % C |  | % H |
|---|---|---|---|
| calculated: | 71.16 | calculated: | 8.53 |
| found: | 70.74 | found: | 8.51 |

Application Example

UV-curable Overprint Varnish (Containing Aminoacrylate)

Compounds, in accordance with the invention were tested for its suitability as a photoinitiator in a UV-curable overprint varnish (OPV) and compared with commercially available initiators. The composition of the OPV can be found in the Table below.

| Component | % by weight |
|---|---|
| Ebecryl 605 | 30.0 |
| Ebecryl 7100 | 10.0 |
| Ebecryl 40 | 5.0 |
| OTA 480 | 30.0 |

-continued

| Component | % by weight |
|---|---|
| TPGDA | 24.0 |
| Ebecryl 1360 | 0.5 |
| Dow Corning 57 | 0.5 |
| Σ | 100.0 |

OTA 480: propoxylated glycerol triacrylate (UCB)
TPGDA: tripropylene glycol diacrylate (UCB)
Ebecryl 605: bisphenol A epoxy acrylate, diluted with 25% TPGDA (UCB)
Ebecryl 7100: amine acrylate (UCB)
Ebecryl 40: propoxylated/ethoxylated pentaerythritol tetraacrylate (UCB)
Ebecryl 1360: silicone hexaacrylate (UCB)
Dow Corning 57: silicone additive, flow improver (Dow Corning)

The samples were applied in a layer thickness of 6 µm to white card using a knife and then cured using a UV irradiation apparatus (2 medium-pressure mercury lamps of 120 W/cm, variable-speed conveyor belt; IST). Immediately after irradiation, the resistance of the coating surface to wiping was determined by means of a paper towel. The curing speed corresponds to that conveyor belt speed of the irradiation apparatus, in m/min, at which the coating surface was assessed as still being resistant to wiping.

In each case, 0.6 g (or 0.8 g) of photoinitiator was included in 10 g of formulation.

| UV irradiation apparatus (IST): | 2 medium-pressure mercury lamps each of 120 W/cm, variable-speed conveyor belt |
|---|---|
| Curing speed: | Determination of the resistance to wiping of the cured clearcoats, given in terms of the conveyor belt speed (in m/min) of the UV irradiation apparatus; thickness of applied layer: 6 µm (Erichson knife apparatus) on card |
| Yellowing/gloss: | Measurement of the b* value 15 minutes after curing (curing at a UV irradiation apparatus conveyor belt speed of 10 m/min); thickness of applied layer: 100 µm (manual knife coater) on white-coated chipboard panels. The measurement angle in the gloss measurement is 20°. |
| Odour rating: | Curing of the clearcoats at previously determined curing speed; thickness of applied layer: 6 µm on aluminium foil. Rating: 0 = odourless, 1 = very weak, 2 = weak, 3 = pronounced, 4 = strong, 5 = very strong. Intrinsic odour of substrate: 1. |

The following Tables show the results for 6% photoinitiator

| Photoinitiator | Curing speed [m/min] | b* | Gloss [%] | Odour rating |
|---|---|---|---|---|
| Irgacure 184 | 50 | 9.2 | 86 | 4 |
| Irgacure 2959 | 50 | 7.5 | 90 | 2 |
| Example 3b | 70 | 8.3 | 89 | 3 |
| Example 3a | 50 | 10.0 | 89 | 2 |

Irgacure 2959: 2-Hydroxy-1-[4-(2-hydroxyethoxy)-phenyl]-2-methyl-propan-1-one (Ciba Specialty Chemicals).
IRGACURE 184: 1-Hydroxy-cyclohexyl-phenyl ketone (Ciba Specialty Chemicals).

The following Tables show the results for 8% photoinitiator

| Photoinitiator | Curing speed [m/min] | b* | Gloss [%] | Odour rating |
|---|---|---|---|---|
| Irgacure 184 | 80 | 9.8 | 90 | 4 |
| Irgacure 2959 | 90 | 19.5 | 89 | 2 |
| Example 3b | 110 | 8.3 | 91 | 2-3 |
| Example 3a | 90 | 11.5 | 91 | 2-3 |

Additional tests are performed using the above referenced overprint varnish but a different UV lamp.

| Cure speed | |
|---|---|
| The maximum velocity of the conveyor of the UV curing equipment, which is required to achieve completely cured varnishes, corresponds to the cure speed (unit: m/min). | |
| PI concentration | 6% |
| Layer thickness | 6 μm |
| Application method | wire bar K Citenco |
| Substrates | white cardboard |
| UV lamp | 1 × 150 W/cm m.p. mercury lamp (IST) with aluminum reflectors |
| Test method | dry rub resistance with paper tissue |

| Yellowing | |
|---|---|
| Photoinitiator concentration | 6% |
| Layer thickness | 100 μm (box bar) |
| Substrate | white chipboard |
| Radiation sources | 1 × 200 W/cm m.p. mercury lamp (IST) aluminum reflectors; additional exposure with fluorescent tube TLK40/05 |
| Cure speed | 10 m/min |
| Measuring device and method | b* (CIE lab), spectrophotometer CM-3600d (Minolta); b* (average of 3 values) after 0, 1, 2, 4, and 22 h of additional UV exposure with Philips TLK 40W/05 |

| Gloss | |
|---|---|
| Photoinitiator concentration | 6% |
| Layer thickness 100 μm (box bar) | |
| Substrate | white chip board |
| Radiation sources | 1 × 200 W/cm m.p. mercury lamp (IST) with dichroic reflector ("cold mirror") |
| Cure speed | 10 m/min |
| Measuring device and method | Haze-Gloss (Byk-Gardner), measuring 15 min after curing, measuring angle 20° |

Results:

| Photoinitiator | Curing speed [m/min] | b* | Gloss [%] |
|---|---|---|---|
| Irgacure 184 | 70 | 7.3 | 87 |
| Irgacure 2959 | 70 | 7.4 | 88 |
| Ex. 3a | 90 | 7.1 | 89 |
| Ex. 3b | 100 | 8.5 | 89 |

-continued

| Photoinitiator | Curing speed [m/min] | b* | Gloss [%] |
|---|---|---|---|
| Ex. 4 | 80 | 6.9 | 88 |
| Ex. 17 | 80 | 1.2 | 88 |
| Ex. 23 | 60 | 7.1 | 87 |
| Ex. 20a | 60 | 7.7 | 84 |
| Ex. 20b | 60 | 9.0 | 88 |

The invention claimed is:

1. A photoinitiator of formula I or II

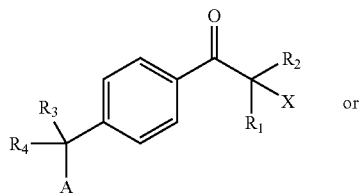

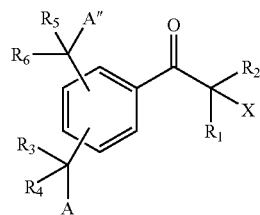

wherein
$R_1$ and $R_2$ are each independently of the other $C_1$-$C_8$alkyl, $C_3$-$C_6$alkenyl, benzyl, —$CH_2$—$C_6H_4$—($C_1$-$C_4$alkyl) or phenyl, or $R_1$ and $R_2$ together are unbranched or branched $C_2$-$C_9$alkylene; and $R_3$, $R_4$, $R_5$ and $R_6$ are each independently of the others hydrogen, $C_1$-$C_8$alkyl, $C_3$-$C_6$alkenyl, benzyl, —$CH_2$—$C_6H_4$—($C_1$-$C_4$alkyl) or phenyl; or $R_3$ and $R_4$ together and/or $R_5$ and $R_6$ together are unbranched or branched $C_3$-$C_9$alkylene;

A is —O—$R_9$,

A" is —O—$R_9$ or hydrogen,

X is —O—$R_{10}$, $R_9$ is hydrogen, —Si($C_1$-$C_6$alkyl)$_3$, $C_1$-$C_{12}$alkyl, $R_{23}$, $C_2$-$C_{18}$acyl, —CO—NH—$C_1$-$C_{12}$alkyl, —CO—$C_1$-$C_4$alkoxy, $C_2$-$C_{20}$hydroxyalkyl, $C_2$-$C_{20}$methoxyalkyl, 3-($C_1$-$C_{18}$alkoxy)-2-hydroxy-propyl, 3-[1,3,3,3-tetramethyl-1-[(trimethylsilyl)oxy]disiloxanyl]-propyl, 2,3-dihydroxy-propyl or linear or branched $C_2$-$C_{21}$hydroxyalkyl or ($C_1$-$C_4$alkoxy)-$C_2$-$C_{21}$alkyl the carbon chain of which is interrupted by from one to nine oxygen atoms, $R_{10}$ is hydrogen, —Si($C_1$-$C_6$alkyl)$_3$, or benzyl, $R_{23}$ is, independently of formula I, a radical

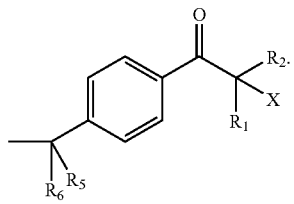

2. A photoinitiator of formula I or II according to claim 1, wherein $R_1$ and $R_2$ are methyl, or $R_1$ and $R_2$ together are $C_5$alkylene;

$R_3$, $R_4$, $R_5$ and $R_6$ are each independently of the others hydrogen, $C_1$-$C_8$alkyl, $C_3$-$C_6$alkenyl, benzyl, —$CH_2$—$C_6H_4$—($C_1$-$C_4$alkyl) or phenyl; or $R_3$ and $R_4$ together and/or $R_5$ and $R_6$ together are unbranched or branched $C_3$-$C_9$alkylene;

A is —O—$R_9$,

A″ is —O—$R_9$, or hydrogen;

X is —OH, $R_9$ for formula I is hydrogen, —Si(CH$_3$)$_3$, $C_1$-$C_8$alkyl, 4-(2-hydroxy-2-methyl-propionyl)-benzyl, 4-(1-hydroxy-cyclohexanecarbonyl)-benzyl, $C_2$-$C_{18}$acyl, —CO—NH—$C_1$-$C_8$alkyl, —CO—$C_1$-$C_4$-alkoxy, $C_2$-$C_{20}$hydroxyalkyl, $C_2$-$C_{20}$methoxyalkyl or $C_2$-$C_{20}$hydroxyalkyl the carbon chain of which is interrupted by from one to nine oxygen atoms;

$R_9$ for formula II is hydrogen, —Si(CH$_3$)$_3$, $C_1$-$C_8$alkyl, 4-(2-hydroxy-2-methyl-propionyl)-benzyl, 2-hydroxymethyl-4-(2-hydroxy-2-methyl-propionyl)-benzyl, 2-methyl-4-(2-hydroxy-2-methyl-propiony)-benzyl, 4-(1-hydroxy-cyclohexanecarbonyl)-benzyl, 2-hydroxymethyl-4-(1-hydroxy-cyclohexanecarbonyl)-benzyl, 2-methyl-4-(1-hydroxy-cyclohexanecarbonyl)-benzyl, $C_2$-$C_{18}$acyl, —CO—NH—$C_1$-$C_8$alkyl, $C_2$-$C_{20}$-hydroxyalkyl, $C_2$-$C_{20}$methoxyalkyl or $C_2$-$C_{20}$hydroxyalkyl the carbon chain of which is interrupted by from one to nine oxygen atoms.

3. A photoinitiator of formula I or II according to claim 2, wherein $R_1$ and $R_2$ are methyl, or $R_1$ and $R_2$ together are $C_5$alkylene;

X is OH;

$R_3$, $R_4$, $R_5$ and $R_6$ are each independently of the others hydrogen or $C_1$-$C_6$alkyl;

$R_3$ and $R_4$ together and/or $R_5$ and $R_6$ together are unbranched or branched $C_4$-$C_9$alkylene;

A is —OH or —O—CH$_3$;

A″ is —OH or —O—CH$_3$ or hydrogen.

4. Photocurable composition comprising (A) at least one ethylenically unsaturated free-radically photopolymerizable compound; and (B) at least one photoinitiator of the formula I or II according to claim 2 or mixtures thereof (C) optionally thermally crosslinkable compounds;

(D) optionally further additives;

(E) optionally further photoinitiators.

5. A pigmented or non-pigmented surface coating, overprint varnish, powder coating, printing ink, inkjet ink, gel coat, composite material or glass fibre coating comprising a composition according to claim 4.

6. A photoinitiator according to claim 1 wherein X is OH.

7. A photoinitiator of formula I

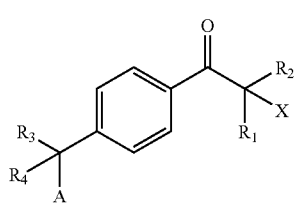

I wherein $R_1$ and $R_2$ are each independently of the other $C_1$-$C_8$alkyl, $C_3$-$C_6$alkenyl, benzyl, —$CH_2$—$C_6H_4$—($C_1$-$C_4$alkyl) or phenyl, or $R_1$ and $R_2$ together are unbranched or branched $C_2$-$C_9$alkylene; and $R_3$ and $R_4$ are each independently of the other hydrogen, $C_1$-$C_8$alkyl, $C_3$-$C_6$alkenyl, benzyl, —$CH_2$—$C_6H_4$—($C_1$-$C_4$alkyl) or phenyl; or $R_3$ and $R_4$ together are unbranched or branched $C_3$-$C_9$alkylene;

A is —O—$R_9$,

X is —O—$R_{10}$, $R_9$ is hydrogen, —Si($C_1$-$C_6$alkyl)$_3$, $C_1$-$C_{12}$alkyl, $R_{23}$, $C_2$-$C_{18}$acyl, —CO—NH—$C_1$-$C_{12}$alkyl, —CO—$C_1$-$C_4$alkoxy, $C_2$-$C_{20}$hydroxyalkyl, $C_2$-$C_{20}$methoxyalkyl, 3-($C_1$-$C_{18}$alkoxy)-2-hydroxy-propyl 3-[1,3,3,3-tetramethyl-1-[(trimethylsilyl)oxy]disiloxanyl]-propyl, 2,3-dihydroxy-propyl or linear or branched $C_2$-$C_{21}$hydroxyalkyl or ($C_1$-$C_4$alkoxy)-$C_2$-$C_{21}$alkyl the carbon chain of which is interrupted by from one to nine oxygen atoms, $R_{10}$ is hydrogen, —Si($C_1$-$C_6$alkyl)$_3$, or benzyl, $R_{23}$ is, independently of formula I, a radical

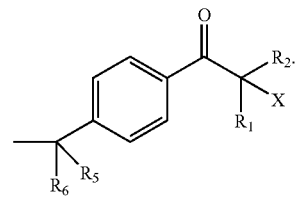

8. A photoinitiator of formula I according to claim 7, wherein $R_1$ and $R_2$ are methyl, or $R_1$ and $R_2$ together are $C_5$alkylene;

$R_3$ and $R_4$ are each independently of the other hydrogen, $C_1$-$C_8$alkyl, $C_3$-$C_6$alkenyl, benzyl, —$CH_2$—$C_6H_4$—($C_1$-$C_4$alkyl) or phenyl; or $R_3$ and $R_4$ together are unbranched or branched $C_3$-$C_9$alkylene;

A is —O—$R_9$,

X is —OH, and $R_9$ is hydrogen, —Si(CH$_3$)$_3$, $C_1$-$C_8$alkyl, 4-(2-hydroxy-2-methyl-propionyl)-benzyl, 4-(1-hydroxy-cyclohexanecarbonyl)-benzyl, $C_2$-$C_{18}$acyl, —CO—NH—$C_1$-$C_8$alkyl, —CO—$C_1$-$C_4$-alkoxy, $C_2$-$C_{20}$hydroxyalkyl, $C_2$-$C_{20}$methoxyalkyl or $C_2$-$C_{20}$hydroxyalkyl the carbon chain of which is interrupted by from one to nine oxygen atoms.

9. A photoinitiator of formula I according to claim 8, wherein $R_1$ and $R_2$ are methyl, or $R_1$ and $R_2$ together are $C_5$alkylene;

X is OH;

$R_3$ and $R_4$ are each independently of the other hydrogen or $C_1$-$C_6$alkyl; or $R_3$ and $R_4$ together are unbranched or branched $C_4$-$C_9$alkylene; and A is —OH or —O—CH$_3$.

* * * * *

UNITED STATES PATENT AND TRADEMARK OFFICE
CERTIFICATE OF CORRECTION

PATENT NO.       : 7,642,296 B2                                              Page 1 of 1
APPLICATION NO.  : 11/578595
DATED            : January 5, 2010
INVENTOR(S)      : Hüsler et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 349 days.

Signed and Sealed this

Sixteenth Day of November, 2010

David J. Kappos
*Director of the United States Patent and Trademark Office*